United States Patent [19]

Fujikawa et al.

[11] Patent Number: 5,026,708
[45] Date of Patent: Jun. 25, 1991

[54] PYRIMIDINE TYPE MEVALONOLACTONES

[75] Inventors: Yoshihiro Fujikawa; Mikio Suzuki; Hiroshi Iwasaki, all of Funabashi; Mitsuaki Sakashita; Masaki Kitahara, both of Saitama, all of Japan

[73] Assignee: Nissan Chemical Industries Ltd., Tokyo, Japan

[21] Appl. No.: 243,468

[22] Filed: Sep. 12, 1988

[30] Foreign Application Priority Data

Sep. 12, 1987 [JP] Japan .................. 62-229357
Jan. 25, 1988 [JP] Japan .................. 63-14027
Jun. 11, 1988 [JP] Japan .................. 63-142695
Aug. 16, 1988 [JP] Japan .................. 63-203381

[51] Int. Cl.⁵ ............... A61K 31/505; C07D 239/26; C07D 407/06; C07D 407/14
[52] U.S. Cl. .................. 514/256; 544/229; 544/333; 544/335
[58] Field of Search ............ 544/296, 333, 334, 335, 544/229; 514/256

[56] References Cited

U.S. PATENT DOCUMENTS 4,681,893  7/1987  Roth ..................... 514/422
4,735,958  4/1988  Roth et al. ............. 31/395
4,868,185  9/1989  Chucholowski et al. .... 514/256

FOREIGN PATENT DOCUMENTS 0307342  3/1989  European Pat. Off.

Primary Examiner—John M. Ford
Attorney, Agent, or Firm—Oblon, Spivak, McClelland, Maier & Neustadt

[57] ABSTRACT

A compound of the formula:

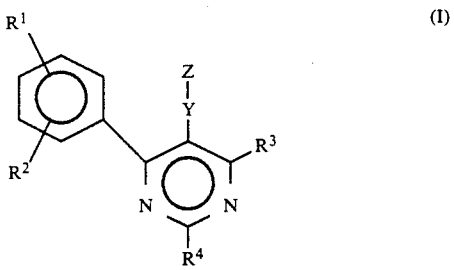

wherein $R^1$ and $R^2$ are independently hydrogen, $C_{1-6}$ alkyl, $C_{3-6}$ cycloalkyl, $C_{1-3}$ alkoxy, n-butoxy, i-butoxy, sec-butoxy, $R^5R^6N$— (wherein $R^5$ and $R^6$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or —O(CH$_2$)$_l$OR$^{15}$ (wherein $R^{15}$ is hydrogen or $C_{1-3}$ alkyl, and l is 1, 2 or 3); or when located at the ortho position to each other, $R^1$ and $R^2$ together form —CH=CH—CH=CH— or methylene dioxy; Y is —CH$_2$—, —CH$_2$CH$_2$—, —CH=CH—, —CH$_2$—CH=CH— or —CH=CH—CH$_2$—; Z is —Q—CH$_2$WCH$_2$—CO$_2$R$^{12}$,

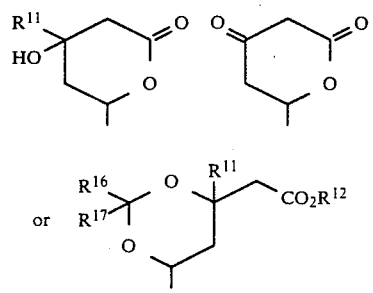

(wherein Q is —C(O)—, —C(OR$^{13}$)$_2$— or —CH(OH)—; W is —C(O)—, —C(OR$^{13}$)$_2$— or —C(R$^{11}$)(OH)—; $R^{11}$ is hydrogen or $C_{1-3}$ alkyl; $R^{12}$ is hydrogen or $R^{14}$ (wherein $R^{14}$ is physiologically hydrolyzable alkyl or M (wherein M is NH$_4$, sodium, potassium, ½ calcium or a hydrate of lower alkylamine, di-lower alkylamine or tri-lower alkylamine)); two $R^{13}$ are independently primary or secondary $C_{1-6}$ alkyl; or two $R^{13}$ together form —(CH$_2$)$_2$— or —(CH$_2$)$_3$—; $R^{16}$ and $R^{17}$ are independently hydrogen or $C_{1-3}$ alkyl; $R^3$ is hydrogen, $C_{1-6}$ alkyl, $C_{2-3}$ alkenyl, $C_{3-6}$ cycloalkyl,

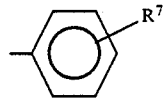

(wherein $R^7$ is hydrogen, $C_{1-4}$ alkyl, $C_{1-3}$ alkoxy, fluoro, chloro, bromo or trifluoromethyl), phenyl—(CH$_2$)$_m$— (wherein m is 1, 2 or 3), —(CH$_2$)$_n$CH(CH$_3$)—phenyl or phenyl—(CH$_2$)$_n$CH(CH$_3$)— (wherein n is 0, 1 or 2): $R^4$ is $C_{1-8}$ alkyl, $C_{3-7}$ cycloalkyl, α- or β-naphthyl, 2—, 3— or 4-pyridyl,

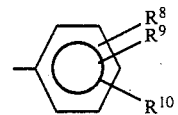

(wherein $R^8$, $R^9$ and $R^{10}$ are independently hydrogen, $C_{1-4}$ alkyl, $C_{1-8}$ alkoxy, $C_{1-3}$ alkylthio, chloro, bromo, fluoro, —NR$^{18}$R$^{19}$ (wherein $R^{18}$ and $R^{19}$ are independently $C_{1-3}$ alkyl), trichloromethyl, trifluoromethyl, trifluoromethoxy, difluoromethoxy, phenoxy, benzyloxy, hydroxy, trimethylsilyloxy, diphenyl-t-butylsilyloxy, hydroxymethyl or —O(CH$_2$)$_k$OR$^{20}$ (wherein $R^{20}$ is hydrogen or $C_{1-3}$ alkyl, and k is 1, 2 or 3); when $R^{10}$ is hydrogen and when located at the ortho position to each other, $R^8$ and $R^9$ together form —OC(R$^{23}$)(R$^{24}$)O— (wherein $R^{23}$ and $R^{24}$ are independently hydrogen or $C_{1-3}$ alkyl)), (Abstract continued on next page.)

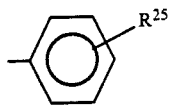
(wherein $R^{25}$ is hydrogen, $C_{1-4}$ alkyl, $C_{1-3}$ alkoxy, chloro, bromo, or fluoro) or $C_{1-3}$ alkyl substituted by 1 member selected from the group consisting of
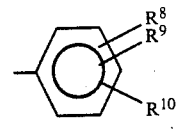
(wherein $R^8$, $R^9$ and $R^{10}$ are as defined above) and naphthyl and by 0, 1 or 2 members selected from the group consisting of $C_{1-8}$ alkyl.
37 Claims, No Drawings

PYRIMIDINE TYPE MEVALONOLACTONES

The present invention relates to novel mevalonolactones having a pyrimidine ring, processes for their production, pharmaceutical compositions containing them and their pharmaceutical uses particularly as anti-hyperlipidemic, hypolipoproteinemic and anti-atherosclerotic agents, and intermediates useful for their production and processes for the production of such intermediates.

Some fermentation metabolic products such as compactine, CS-514, Mevinolin or semi-synthetic derivatives or fully synthetic derivatives thereof are known to be inhibitors against HMG-CoA reductase which is a rate limiting enzyme for cholesterol biosynthesis. (A. Endo J. Med Chem., 28(4) 401 (1985))

CS-514 and Mevinolin have been clinically proved to be potentially useful anti-hyperlipoproteinemic agents, and they are considered to be effective for curing or preventing diseases of coronary artery sclerosis or atherosclerosis. (IXth Int. Symp. Drugs Affect. Lipid Metab., 1986, p30, p31, p66)

However, with respect to fully synthetic derivatives, particularly hetero aromatic derivatives of inhibitors against HMG-CoA reductase, limited information is disclosed in the following literatures:

WPI ACC NO. 84-158675, 86-028274, 86-098816, 86-332070, 87-124519, 87-220987, 88-07781, 88-008460, 88-091798 and 88-112505.

The present inventors have found that mevalonolactone derivatives having a pyrimidine ring, the corresponding dihydroxy carboxylic acids and salts and esters thereof have high inhibitory activities against cholesterol biosynthesis wherein HMG-CoA reductase acts as a rate limiting enzyme. The present invention has been accomplished on the basis of this discovery.

The novel mevalonolactone derivatives of the present invention are represented by the following formula I:

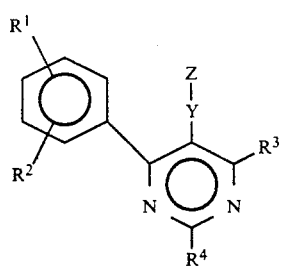

wherein $R^1$ and $R^2$ are independently hydrogen, $C_{1-6}$ alkyl, $C_{3-6}$ cycloalkyl, $C_{1-3}$ alkoxy, n-butoxy, i-butoxy, sec-butoxy, $R^5R^6N-$ (wherein $R^5$ and $R^6$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{15}$ (wherein $R^{15}$ is hydrogen or $C_{1-3}$ alkyl, and l is 1, 2 or 3); or when located at the ortho position to each other, $R^1$ and $R^2$ together form $-CH=CH-CH=CH-$ or methylene dioxy; Y is $-CH_2-$, $-CH_2CH_2-$, $-CH=CH-$, $-CH_2-CH=CH-$ or $-CH=CH-CH_2-$; Z is $-Q-CH_2WCH_2-CO_2R^{12}$,

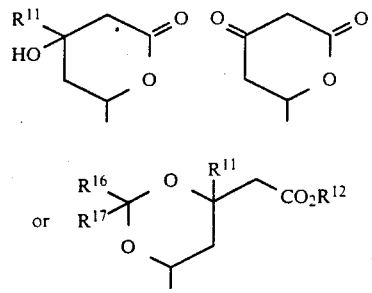

(wherein Q is $-C(O)-$, $-C(OR^{13})_2-$ or $-CH(OH)-$; W is $-C(O)-$, $-C(OR^{13})_2-$ or $-C(R^{11})(OH)-$; $R^{11}$ is hydrogen or $C_{1-3}$ alkyl; $R^{12}$ is hydrogen or $R^{14}$ (wherein $R^{14}$ is physiologically hydrolyzable alkyl or M (wherein M is $NH_4$, sodium, potassium, ½ calcium or a hydrate of lower alkylamine, di-lower alkylamine or tri-lower alkylamine)); two $R^{13}$ are independently primary or secondary $C_{1-6}$ alkyl; or two $R^{13}$ together form $-(CH_2)_2-$ or $-(CH_2)_3-$; $R^{16}$ and $R^{17}$ are independently hydrogen or $C_{1-3}$ alkyl; $R^3$ is hydrogen, $C_{1-6}$ alkyl, $C_{2-3}$ alkenyl, $C_{3-6}$ cycloalkyl,

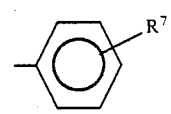

(wherein $R^7$ is hydrogen, $C_{1-4}$ alkyl, $C_{1-3}$ alkoxy, fluoro, chloro, bromo or trifluoromethyl), phenyl-$(CH_2)_m-$ (wherein m is 1, 2 or 3), $-(CH_2)_nCH(CH_3)$-phenyl or phenyl-$(CH_2)_nCH(CH_3)-$ (wherein n is 0, 1 or 2); $R^4$ is $C_{1-8}$ alkyl, $C_{3-7}$ cycloalkyl, α or β-naphthyl, 2-, 3- or 4-pyridyl,

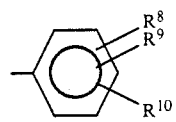

(wherein $R^8$, $R^9$ and $R^{10}$ are independently hydrogen, $C_{1-4}$ alkyl, $C_{1-8}$ alkoxy, $C_{1-3}$ alkylthio, chloro, bromo, fluoro, $-NR^{18}R^{19}$ (wherein $R^{18}$ and $R^{19}$ are independently $C_{1-3}$ alkyl), trichloromethyl, trifluoromethyl, trifluoromethoxy, difluoromethoxy, phenoxy, benzyloxy, hydroxy, trimethylsilyloxy, diphenyl-t-butylsilyloxy, hydroxymethyl or $-O(CH_2)_kOR^{20}$ (wherein $R^{20}$ is hydrogen or $C_{1-3}$ alkyl, and k is 1, 2 or 3); when $R^{10}$ is hydrogen and when located at the ortho position to each other, $R^8$ and $R^9$ together optionally form $-OC(R^{23})(R^{24})O-$ (wherein $R^{23}$ and $R^{24}$ are independently hydrogen or $C_{1-3}$ alkyl), when $R^9$ and $R^{10}$ are hydrogen at the same time, $R^8$ is

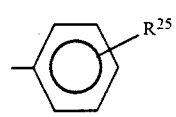

(wherein $R^{25}$ is hydrogen, $C_{1-4}$ alkyl, $C_{1-3}$ alkoxy, chloro, bromo, or fluoro), or $C_{1-3}$ alkyl substituted by 1 member selected from the group consisting of

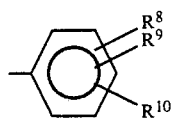

(wherein $R^8$, $R^9$ and $R^{10}$ are as defined above) and naphthyl and by 0, 1 or 2 members selected from the group consisting of $C_{1-8}$ alkyl.

Various substituents in the formula I will be described in detail with reference to specific examples However, it should be understood that the present invention is by no means restricted by such specific examples.

$C_{1-6}$ alkyl for $R^1$ and $R^2$ includes, for example, methyl, ethyl, n-propyl, i-propyl, n-butyl, i-butyl, sec-butyl, t-butyl and n-hexyl. $C_{1-3}$ alkoxy for $R^1$ and $R^2$ includes, for example, methoxy, ethoxy, n-propoxy and i-propoxy.

$C_{1-3}$ alkyl for $R^{11}$ includes, for example, methyl, ethyl, n-propyl and i-propyl.

Specific examples for $R^{13}$ include, for example, methyl, ethyl, n-propyl, i-propyl, n-butyl, i-butyl, n-pentyl and n-hexyl.

When M is a metal capable of forming a pharmaceutically acceptable salt, it includes, for example, sodium and potassium.

$CO_2M$ includes, for example, $-CO_2NH_4$ and $-CO_2H$. (primary to tertiary lower alkylamine such as trimethylamine).

$C_{1-6}$ alkyl for $R^3$ includes, for example, methyl, ethyl, n-propyl, i-propyl, n-butyl, i-butyl, sec-butyl, t-butyl, n-pentyl and n-hexyl.

$C_{2-3}$ alkenyl for $R^3$ includes, for example, vinyl and i-propenyl.

$C_{3-6}$ cycloalkyl for $R^3$ includes, for example, cyclopropyl, cyclobutyl, cyclopentyl and cyclohexyl.

Phenyl-$(CH_2)_m$—, $-(CH_2)_nCH(CH_3)$-phenyl and $-CH(CH_3)(CH_2)n$-phenyl for $R^3$ include, for example, benzyl, α-phenylethyl, β-phenylethyl, β-phenylpropyl, γ-phenylpropyl, 1-methyl-2-phenylethyl, 1-methyl-3-phenylpropyl and γ-phenylbutyl.

$C_{1-8}$ alkyl for $R^4$ includes, for example, methyl, ethyl, n-propyl, i-propyl, n-butyl, i-butyl, sec-butyl, t-butyl, n-pentyl, n-hexyl, n-heptyl and n-octyl.

$C_{1-4}$ for $R^8$, $R^9$ and $R^{10}$ includes, for example, methyl, ethyl, n-propyl, i-propyl, n-butyl, sec-butyl, i-butyl and t-butyl.

$C_{1-8}$ alkoxy for $R^8$, $R^9$ and $R^{10}$ includes, for example, methoxy, ethoxy, n-propoxy, i-propoxy, n-butoxy and n-octyloxy.

$C_{1-3}$ alkyl for $R^{18}$ and $R^{19}$ includes, for example, methyl, ethyl, n-propyl and i-propyl.

$C_{1-4}$ alkyl for $R^{25}$ includes, for example, methyl, ethyl, n-propyl, i-propyl, n-butyl, sec-butyl, i-butyl and t-butyl.

$C_{1-3}$ alkoxy for $R^{25}$ includes, for example, methoxy, ethoxy, n-propoxy and i-propoxy.

Further, these compounds may have at least one or two asymmetric carbon atoms and may have at least two to four optical isomers. The compounds of the formula I include all of these optical isomers and all of the mixtures thereof.

Among compounds having carboxylic acid moieties falling outside the definition of $-CO_2R^{12}$ of the carboxylic acid moiety of substituent Z of the compounds of the present invention, those which undergo physiological hydrolysis, after intake, to produce the corresponding carboxylic acids (compounds wherein the $-CO_2R^{12}$ moiety is $-CO_2H$) are equivalent to the compounds of the present invention.

Now, preferred substituents of the compounds of the present invention will be described.

In the following preferred, more preferred, still further preferred and most preferred examples, the numerals for the positions of the substituents indicate the positions on the pyrimidine ring.

As preferred examples for $R^1$ and $R^2$, when $R^2$ is hydrogen, $R^1$ is hydrogen, 3'-fluoro, 3'-chloro, 3'-methyl, 4'-methyl, 4'-chloro and 4'-fluoro.

Other preferred combinations of $R^1$ and $R^2$ include 3'-methyl-4'-chloro, 3',5'-dichloro, 3',5'-difluoro, 3',5'-dimethyl and 3'-methyl-4'-fluoro.

Preferred examples for $R^3$ include primary and secondary $C_{1-6}$ alkyl and $C_{3-6}$ cycloalkyl.

Preferred examples for $R^4$ include $C_{1-8}$ alkyl, $C_{3-7}$ cycloalkyl, α- or β-naphthyl, 2-, 3- or 4-pyridyl,

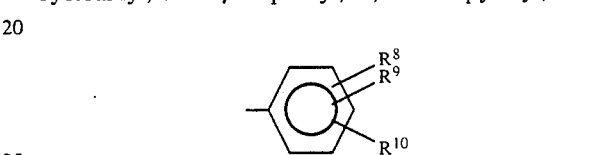

(wherein $R^8$, $R^9$ and $R^{10}$ are independently hydrogen, $C_{1-4}$ alkyl, $C_{1-8}$ alkoxy, chloro, bromo, fluoro, dimethylamino, trifluoromethyl, hydroxy, phenoxy, benzyloxy, trimethylsilyloxy, diphenyl-t-butylsilyloxy, methylenedioxy (in this case, $R^{10}$ is hydrogen), hydroxymethyl or when $R^9$ and $R^{10}$ are hydrogen at the same time, $R^8$ is

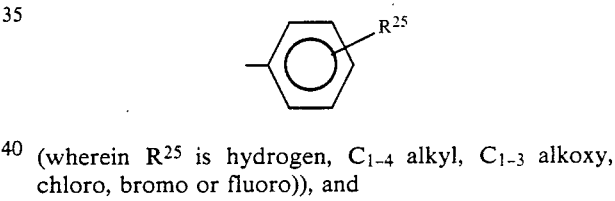

(wherein $R^{25}$ is hydrogen, $C_{1-4}$ alkyl, $C_{1-3}$ alkoxy, chloro, bromo or fluoro)), and

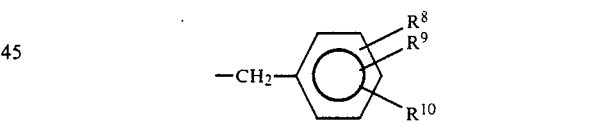

(wherein $R^8$, $R^9$ and $R^{10}$ have the same meanings as in the case of the above preferred examples).

Preferred examples for Y include $-CH_2-CH_2-$ and $-CH=CH-$.

Preferred examples for Z include

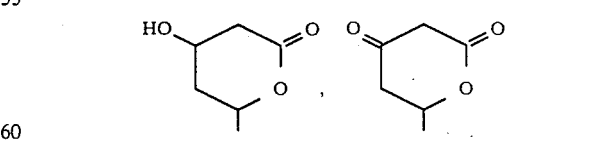

$-CH(OH)CH_2CH(OH)CH_2CO_2R^{12}$, $-CH(OH)CH_2C(O)CH_2CO_2R^{12}$ and $-CH(OH)CH_2C(OR^{13})_2CH_2CO_2R^{12}$.

Now, more preferred substituents of the compounds of the present invention will be described.

As more preferred examples for $R^1$ and $R^2$, when $R^2$ is hydrogen $R^1$ is hydrogen, 4'-methyl, 4'-chloro or 4'-fluoro. When both R¹ and R² are not hydrogen, they together represent 3',5'-dimethyl or 3'-methyl-4'-fluoro.

As more preferred examples for R³, the above-mentioned preferred examples of R³ may be mentioned.

As more preferred examples for R⁴, the above-mentioned preferred examples for R⁴ except $C_{1-8}$ alkyl, $C_{3-7}$ alkyl, cycloalkyl, α- or β-naphthyl, and 2-, 3- or 4-pyridyl, may be mentioned.

As more preferred examples for Y, —CH₂—CH₂— and (E)—CH=CH— may be mentioned.

As more preferred examples for Z, the above preferred examples for Z may be mentioned.

Now, still further preferred substituents of the compounds of the present invention will be described.

As still further preferred examples for R¹ and R², when R² is hydrogen, R¹ is hydrogen, 4'-chloro or 4'-fluoro, or R¹ and R² together represent 3'-methyl-4'-fluoro.

Still further preferred examples for R³ include ethyl, n-propyl, i-propyl and cyclopropyl.

Still further preferred examples for R⁴ include

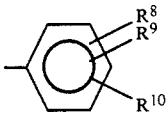

(wherein R⁸, R⁹ and R¹⁰ are independently hydrogen, methyl, ethyl, n-propyl, i-propyl, n-butyl, t-butyl, methoxy, ethoxy, n-propoxy, i-propoxy, chloro, bromo, fluoro, trifluoromethyl, hydroxy, trimethylsilyloxy, diphenyl-t-butylsilyloxy, methylenedioxy (in this case, R¹⁰ is hydrogen), hydroxymethyl or phenyl), and benzyl.

Still further preferred examples for Y include (E)- —CH=CH—.

As still further preferred examples for Z, the above-mentioned preferred example for Z may be mentioned.

Now, the most preferred substituents for the compounds of the present invention will be described.

As the most preferred examples for R¹ and R², R² is hydrogen and R¹ is hydrogen, 4'-chloro or 4'-fluoro.

The most preferred examples for R³ include i-propyl and cyclopropyl.

The most preferred examples for R⁴ include phenyl, 3'-chlorophenyl, 4'-chlorophenyl, 3'-tolyl, 4'-tolyl, 3'-methoxyphenyl, 4'-methoxyphenyl, 3'-trifluoromethylphenyl, 4'-trifluoromethylphenyl, and 3',4'-dimethoxyphenyl.

The most preferred example for Y may be (E)- —CH=CH—.

As the most preferred examples for Z, the above-mentioned preferred examples for Z may be mentioned.

Now, particularly preferred specific compounds of the present invention will be presented. The following compounds (a) to (z) are shown in the form of carboxylic acids. However, the present invention includes not only the compounds in the form of carboxylic acids but also the corresponding lactones formed by the condensation of the carboxylic acids with hydroxy at the 5-position, and sodium salts and lower alkyl esters (such as methyl, ethyl, i-propyl and n-propyl esters) of the carboxylic acids, which can be physiologically hydrolyzed to the carboxylic acids.

(a) (E)-3,5-dihydroxy-7-[4'-(4''-fluorophenyl)-6'-(1''-methylethyl)-2 '-(4''-tolyl)pyrimidin-5'-yl]hept-6-enoic acid (b) (E)-3,5-dihydroxy-7-[4'-(4''-fluorophenyl)-6'-(1''-methylethyl)-2 '-phenylpyrimidin-5'yl]hept-6-enoic acid (c) (E)-3,5-dihydroxy-7-[2'-(3''-chlorophenyl)-4'-(4''-fluorophenyl)-6 '-(1''-methylethyl)pyrimidin-5'yl]-hept-6-enoic acid (d) (E)-3,5-dihydroxy-7-[4'-(4''-fluorophenyl)-2'-(4''-methoxyphenyl)-6 '-(1''-methylethyl)pyrimidin-5'-yl]hept-6-enoic acid (e) (E)-3,5-dihydroxy-7-[4'-(4''-fluorophenyl)-6'-(1''-methylethyl)-2 '-(3''-trifluoromethylphenyl)-pyrimidin-5'-yl]hept-6-enoic acid (f) (E)-3,5-dihydroxy-7-[4'-cyclopropyl-6'-(4''-fluorophenyl)-2'-(4''-tolyl)pyrimidin-5'-yl]hept-6-enoic acid (g) (E)-3,5-dihydroxy-7-[4'-cyclopropyl-6'-(4''-fluorophenyl)-2'-phenylpyrimidin-5 '-yl]hept-6-enoic acid (h) (E)-3,5-dihydroxy-7-[2'-(3''-chlorophenyl)-4'-cyclopropyl-6'-(4''fluorophenyl)pyrimidin-5'-yl]hept-6-enoic acid (i) (E)-3,5-dihydroxy-7-[4'-cyclopropyl-6'-(4''-fluorophenyl)-2'-(4''-methoxyphenyl)pyrimidin-5'-yl]-hept-6-enoic acid (j) (E)-3,5-dihydroxy-7-[4'-cyclopropyl-6'-(4''-fluorophenyl)-2'-(3''-trifluoromethylphenyl)pyrimidin-5'-yl]hept-6-enoic acid (k) (E)-3,5-dihydroxy-7-[4'-(1''-methylethyl)-6'-phenyl-2'-(4''-tolyl) pyrimidin-5'-yl]hept-6-enoic acid (l) (E)-3,5-dihydroxy-7-[2',6'-diphenyl-4'-(1''-methylethyl) pyrimidin-5'-yl]hept-6-enoic acid (m) (E)-3,5-dihydroxy-7-[2'-(3''-chlorophenyl)-4'-(1''-methylethyl)-6 '-phenylpyrimidin-5'-yl]hept-6-enoic acid (n) (E)-3,5-dihydroxy-7-[2'-(4''-methoxyphenyl)-4'-(1''-methylethyl-6 '-phenylpyrimidin-5'-yl]hept-6-enoic acid (o) (E)-3,5-dihydroxy-7-[4'-(1''-methylethyl)-6'-phenyl-2'-3''-trifluoromethylphenyl)pyrimidin-5'-yl]-hept-6-enoic acid (p) (E)-3,5-dihydroxy-7-4'-(cyclopropyl-6'-phenyl-2'-(4''-tolyl)pyrimidin-5 '-yl]hept-6-enoic acid (q) (E)-3,5-dihydroxy-7-(4'-cyclopropyl-2',6'-diphenylpyrimidin-5'-yl]hept-6-enoic acid (r) (E)-3,5-dihydroxy-7-[2'-(3''-chlorophenyl)-4'-cyclopropyl-6'-phenylpyrimidin-5 '-yl]hept-6enoic acid (s) (E)-3,5-dihydroxy-7-[4'-cyclopropyl-2'-(4''-methoxyphenyl)-6'-phenylpyrimidin-5 '-yl]hept-6-enoic acid (t) (E)-3,5-dihydroxy-7-[4'-cyclopropyl-6'-phenyl-2'-(3''-trifluoromethylphenyl) pyrimidin-5'-yl]hept-6-enoic acid (u) (E)-3,5-dihydroxy-7-[4'-(4''-chlorophenyl)-6'-(1''-methylethyl)-2 '-(4''-tolyl)pyrimidin-5'-yl]hept-6-enoic acid (v) (E)-3,5-dihydroxy-7-[4'-(4''-chlorophenyl)-6'-(1''-methylethyl)-2 '-phenylpyrimidin-5'-yl]hept-6-enoic acid (w) (E)-3,5-dihydroxy-7-[2'-(3''-chlorophenyl)-4'-(4''-chlorophenyl)-6 '-(1''-methylethyl)pyrimidin-5'-yl]hept-6-enoic acid (x) (E)-3,5-dihydroxy-7-[4'-(4''-chlorophenyl)-6'-cyclopropyl-2'-(4''-tolyl)pyrimidin-5'-yl]hept-6-enoic acid (y) (E)-3,5-dihydroxy-7-[4'-(4''-chlorophenyl)-6'-cyclopropyl-2'-phenylpyrimidin-5 '-yl]hept-6-enoic acid (z) (E)-3,5-dihydroxy-7-[2'-(3''-chlorophenyl)-4'-(4''-chlorophenyl)-6 '-cyclopropylpyrimidin-5'-yl]hept-6-enoic acid The mevalonolactones of the formula I can be prepared by the following reaction scheme. The enal III can also be prepared by processes L and M.
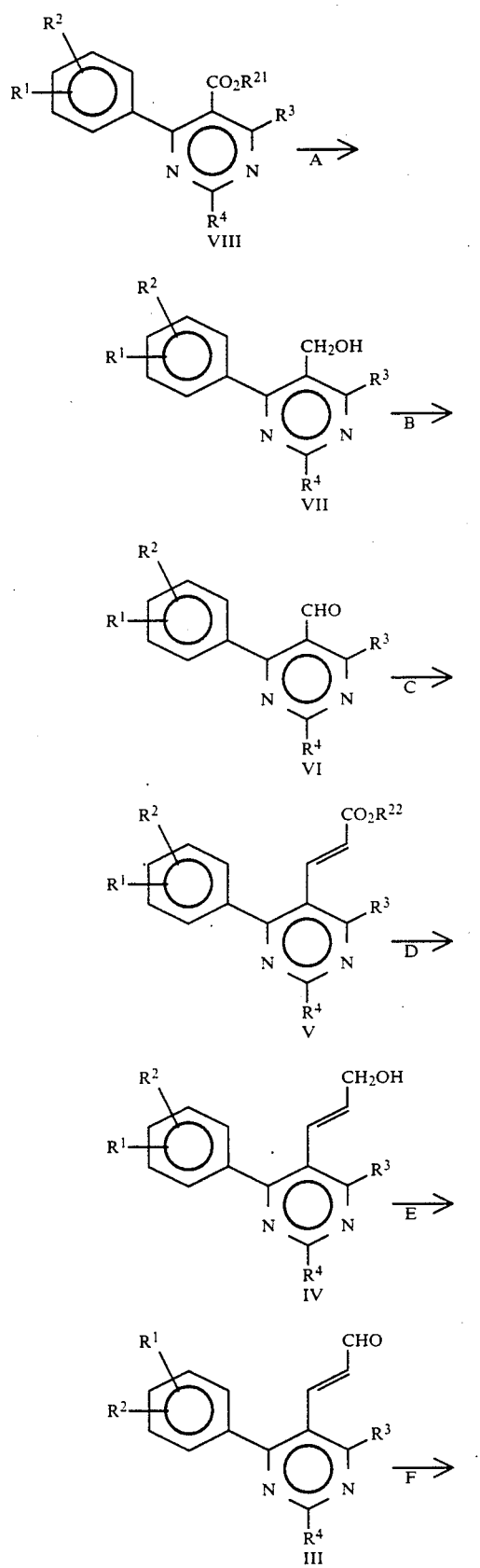
-continued
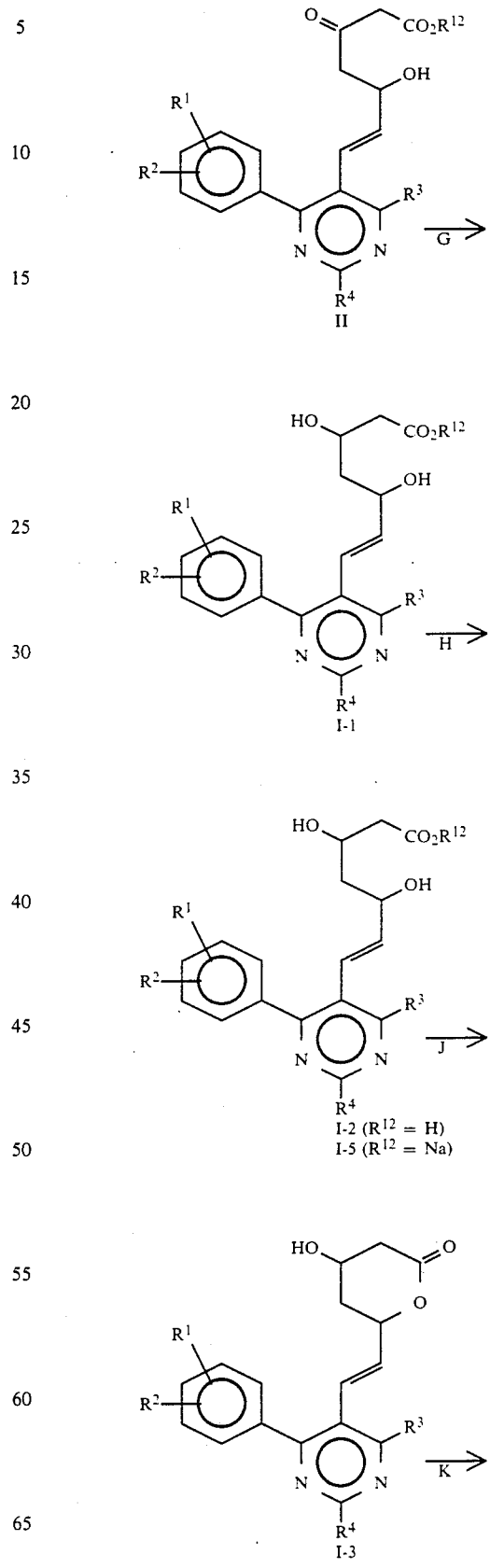
I-2 (R$^{12}$ = H)
I-5 (R$^{12}$ = Na)

-continued

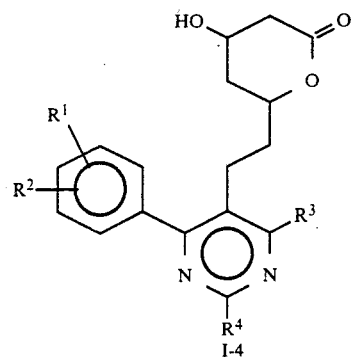
I-4

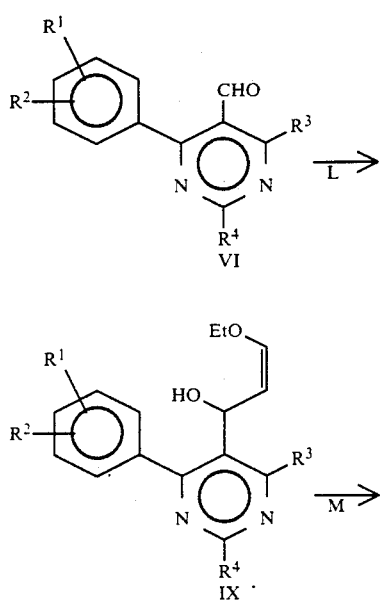
VI
↓ L

IX
↓ M

III

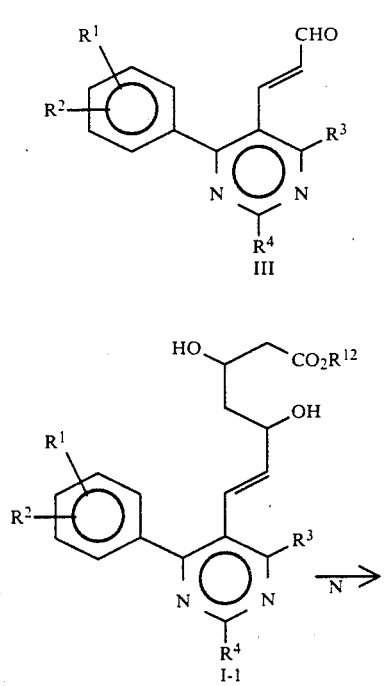
I-1
↓ N

-continued

I-6

In the above reaction scheme, $R^1$, $R^2$, $R^3$, $R^4$, and $R^{12}$ are as defined above with respect to the formula I, and $R^{21}$ and $R^{22}$ independently represent $C_{1-4}$ lower alkyl such as methyl, ethyl, n-propyl, i-propyl or n-butyl.

Step A represents a reduction reaction of the ester to a primary alcohol. Such reduction reaction can be conducted by using various metal hydrides, preferably diisobutylaluminium hydride, in a solvent such as tetrahydrofuran or toluene at a temperature of from $-20°$ to $20°$ C., preferably from $-10°$ to $10°$ C.

Step B represents an oxidation reaction of the primary alcohol to an aldehyde, which can be conducted by using various oxidizing agents. Preferably, the reaction can be conducted by using pyridinium chlorochromate in methylene chloride at a temperature of from $0°$ to $25°$ C., or by using oxalyl chloride, dimethyl sulfoxide and a tertiary amine such as triethylamine (Swern oxidation), or by using a sulfur trioxide pyridine complex.

Step C represents a reaction for the synthesis of an $\alpha,\beta$-unsaturated carboxylic acid ester, whereby a transform $\alpha,\beta$-unsaturated carboxylic acid ester can be obtained by a so-called Horner-Wittig reaction by using an alkoxycarbonylmethyl phosphonate. The reaction is conducted by using sodium hydride or potassium t-butoxide as the base in dry tetrahydrofuran at a temperature of from $-30°$ to $0°$ C., preferably from $-20°$ to $-15°$ C.

Step D represents a reduction reaction of the $\alpha,\beta$-unsaturated carboxylic acid ester to an allyl alcohol. This reduction reaction can be conducted by using various metal hydrides, preferably diisobutylaluminiumhydride, in a solvent such as dry tetrahydrofuran or toluene at a temperature of from $-10°$ to $10°$ C., preferably from $-10°$ to $0°$ C.

Step E represents an oxidation reaction of the allyl alcohol to an enal. This oxidation reaction can be conducted by using various oxidizing agents, particularly active manganese dioxide, in a solvent such as tetrahydrofuran, acetone, ethyl ether or ethyl acetate at a temperature of from $0°$ to $100°$ C., preferably from $15°$ to $50°$ C.

Step F represents a double anion condensation reaction between the enal III and an acetoacetate. Such condensation reaction is preferably conducted by using sodium hydride and n-butyl lithium as the base in tetrahydrofuran at a temperature of from $-80°$ to $0°$ C, preferably from $-30°$ to $-10°$ C.

Step G represents a reduction reaction of the carbonyl group, which can be conducted by using a metal hydride, preferably sodium borohydride in ethanol at a temperature of from '10° to 25° C., preferably from −10° to 5° C. Further, the reduction reaction may be conducted by using zinc borohydride in dry ethyl ether or dry tetrahydrofuran at a temperature of −100° to 25° C., preferably from −80° to −50° C.

Step H is a step for hydrolyzing the ester. The hydrolysis can be conducted by using an equimolar amount of a base, preferably potassium hydroxide or sodium hydroxide, in a solvent mixture of water and methanol or ethanol at a temperature of from 10° to 25° C. The free acid hereby obtained may be converted to a salt with a suitable base.

Step J is a step for forming a mevalonolactone by the dehydration reaction of the free hydroxy acid I-2. The dehydration reaction can be conducted in benzene or toluene under reflux while removing the resulting water or by adding a suitable dehydrating agent such as molecular sieve.

Further, the dehydration reaction may be conducted in dry methylene chloride by using a lactone-forming agent such as carbodiimide, preferably a water soluble carbodiimide such as N-cyclohexyl-N'-[2'-(methylmorpholinium)ethyl]carbodiimide p-toluene sulfonate at a temperature of from 10° to 35° C., preferably from 20° to 25° C.

Step K represents a reaction for hydrogenating the double bond connecting the mevalonolactone moiety and the pyrimidine ring. This hydrogenation reaction can be conducted by using a catalytic amount of palladium-carbon or rhodium-carbon in a solvent such as methanol, ethanol, tetrahydrofuran or acetonitrile at a temperature of from 0° to 50° C., preferably from 10° to 25° C.

Step L represents a synthesis of a 3-ethoxy-1-hydroxy-2-propene derivative, which can be prepared by reacting a compound VI to lithium compound which has been preliminarily formed by treating cis-1-ethoxy-2-(tri-n-butylstannyl)ethylene with butyl lithium in tetrahydrofuran.

As the reaction temperature, it is preferred to employ a low temperature at a level of from −60° to −78° C.

Step M represents a synthesis of an enal by acidic hydrolysis. As the acid catalyst, it is preferred to employ p-toluene sulfonic acid, hydrochloric acid or sulfuric acid, and the reaction may be conducted in a solvent mixture of water and tetrahydrofuran or ethanol at a temperature of from 10° to 25° C. The 3-ethoxy-1-hydroxy-2-propene derivative obtained in Step L can be used in Step M without purification i.e. by simply removing tetra-n-butyl tin formed simultaneously.

Step N represents a reaction for the synthesis of an α,β-unsaturated ketone by the selective oxidation of the dihydroxy carboxylic acid ester. This reaction can be conducted by using activated manganese dioxide in a solvent such as ethyl ether, tetrahydrofuran, benzene or toluene at a temperature of from 20° to 80° C., preferably from 40° to 80° C.

In addition to the compounds disclosed in Examples given hereinafter, compounds of the formulas I-2 and I-5 given in Table 1 can be prepared by the process of the present invention. In Table 1, n- means normal, i- means iso, sec- means secondary and cyclo- means cyclo. Likewise, Me means methyl, Et means ethyl, Pr means propyl, Bu means butyl, Pent means pentyl, Hex means hexyl and Ph means phenyl.

TABLE 1

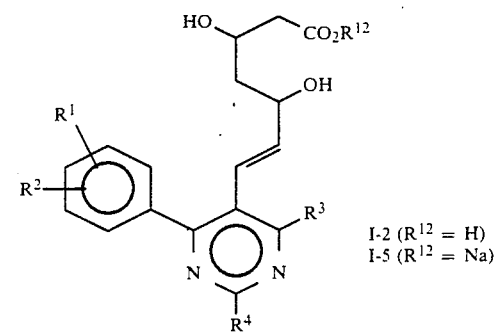

I-2 ($R^{12}$ = H)
I-5 ($R^{12}$ = Na)

| $R^1$ | $R^2$ | $R^3$ | $R^4$ |
|---|---|---|---|
| 3-Me | 4-Me | Me | Ph |
| 3-Me | 4-F | Me | Ph |
| 4-MeO | H | Me | Ph |
| 4-PhO | H | Me | Ph |
| 4-PhCH$_2$O | H | Me | Ph |
| 4-F | H | Me | 4-F—Ph |
| 4-F | H | i-Pr | 2-Me—Ph |
| 4-F | H | i-Pr | 3-Me—Ph |
| 4-F | H | i-Pr | 2-Cl—Ph |
| 4-F | H | i-Pr | 3-Cl—Ph |
| 4-F | H | i-Pr | 3,4-diCl—Ph |
| 4-F | H | i-Pr | 3,5-diCl—Ph |
| 4-F | H | i-Pr | 2-MeO—Ph |
| 4-F | H | i-Pr | 3-MeO—Ph |
| 4-F | H | i-Pr | 3,4-diMeO—Ph |
| 4-F | H | i-Pr | 3,5-diMeO—Ph |
| 4-F | H | i-Pr | 4-pyridyl |
| 4-F | H | i-Pr | 3-CF$_3$—Ph |
| 4-F | H | i-Pr | 4-HO—Ph |
| 4-F | H | i-Pr | 4-Me$_2$N—Ph |
| 4-F | H | cyclo-Pr | 4-Cl—Ph |
| 4-F | H | Et | Ph |
| 4-F | H | cyclo-Bu | Ph |

TABLE 1-continued

I-2 (R$^{12}$ = H)
I-5 (R$^{12}$ = Na)

| R$^1$ | R$^2$ | R$^3$ | R$^4$ |
|---|---|---|---|
| 4-F | H | sec-Bu | Ph |
| 4-F | H | i-Bu | Ph |
| 4-F | H | cyclo-Pent | Ph |
| 4-F | H | Me | 4-Ph—Ph |
| 3-MeO | 4-MeO | cyclo-Pr | Ph |
| 4-CF$_3$ | H | cyclo-Pr | Ph |
| 4-i-Pr | H | cyclo-Pr | Ph |
| 4-F | H | cyclo-Pr | 3-pyridyl |
| 4-PhCH$_2$ | H | cyclo-Pr | Ph |
| 4-Cl | H | cyclo-Pr | Ph |
| 4-F | H | cyclo-Hex | Ph |
| 4-F | H | cyclo-Pr | 3,4-diMe—Ph |
| 4-Ph | H | cyclo-Pr | Ph |
| 4-F | H | cyclo-Pr | cyclo-Hexyl |
| 4-F | H | Me | CH$_2$Ph |
| 4-F | H | Me | 4-Me—Ph |
| 4-F | H | Me | 4-MeO—Ph |
| 4-F | H | Me | 1-Naphthyl |
| 2,3-(—CH=CH—CH=CH—) | | cyclo-Pr | Ph |
| 3-Me | 4-Me | i-Pr | Ph |
| 3-Me | 5-Me | i-Pr | Ph |
| 3-Me | 4-F | i-Pr | Ph |
| 4-Cl | H | i-Pr | 3-CF$_3$—Ph |
| 4-Cl | H | i-Pr | 4-MeO—Ph |
| 4-Cl | H | i-Pr | 4-Me—Ph |
| 4-Cl | H | i-Pr | 4-Cl—Ph |
| 4-Cl | H | i-Pr | 4-Ph—Ph |
| 4-MeO | H | i-Pr | Ph |
| 4-PhO | H | i-Pr | Ph |
| 4-PhCH$_2$O | H | i-Pr | Ph |
| 4-F | H | i-Pr | 4-F—Ph |
| 4-F | H | i-Pr | 4-Ph—Ph |
| 3-MeO | 4-MeO | i-Pr | Ph |
| 4-CF$_3$ | H | i-Pr | Ph |
| 4-i-Pr | H | i-Pr | Ph |
| 4-F | H | i-Pr | t-Bu |
| 4-F | H | i-Pr | 3-pyridyl |
| 4-PhCH$_2$ | H | i-Pr | Ph |
| 4-Cl | H | i-Pr | Ph |
| 4-Br | H | i-Pr | Ph |
| 4-F | H | i-Pr | 3,4-diMe—Ph |
| 4-Ph | H | i-Pr | Ph |
| 4-F | H | i-Pr | 4-Cl—Ph |
| 4-F | H | i-Pr | cyclo-Hexyl |
| 4-F | H | i-Pr | CH$_2$Ph |
| 4-F | H | i-Pr | 4-MeO—Ph |
| 4-F | H | i-Pr | 1-Naphthyl |
| 4-F | H | CH$_2$=CH— | Ph |
| 4-F | H | CH(CH$_3$)=CH— | Ph |
| 2,3-(—CH=CH—CH=CH—) | | i-Pr | Ph |
| 4-F | H | i-Pr | n-Hexyl |
| 4-F | H | cyclo-Pr | n-Hexyl |
| 4-Cl | H | cyclo-Pr | 3-CF$_3$—Ph |
| 4-Cl | H | cyclo-Pr | 4-MeO—Ph |
| 4-Cl | H | cyclo-Pr | 4-Me—Ph |
| 4-Cl | H | cyclo-Pr | 4-Cl—Ph |
| 4-Cl | H | cyclo-Pr | 4-Ph—Ph |
| 4-F | H | i-Pr | 3,4,5-tri-MeO—Ph |
| 4-F | H | i-Pr | 4-CF$_3$—Ph |
| 4-Cl | H | i-Pr | 3-Cl—Ph |
| 4-Cl | H | i-Pr | 3-Me—Ph |
| 4-Cl | H | i-Pr | 3-MeO—Ph |
| 4-Cl | H | i-Pr | 3,4-di-MeO—Ph |
| 4-Cl | H | i-Pr | 4-CF$_3$—Ph |

TABLE 1-continued $$\text{Structure with } R^1, R^2 \text{ on phenyl ring, pyrimidine with } R^3, R^4, \text{ and side chain } HO-CH(CH_2-CH(OH)-CH_2-CO_2R^{12})-CH=CH-$$

I-2 ($R^{12}$ = H)
I-5 ($R^{12}$ = Na)

| $R^1$ | $R^2$ | $R^3$ | $R^4$ |
|---|---|---|---|
| 4-Cl | H | i-Pr | Ph |
| H | H | i-Pr | 3-Cl—Ph |
| H | H | i-Pr | 4-Cl—Ph |
| H | H | i-Pr | 3-Me—Ph |
| H | H | i-Pr | 4-Me—Ph |
| H | H | i-Pr | 3-MeO—Ph |
| H | H | i-Pr | 4-MeO—Ph |
| H | H | i-Pr | 3,4-di-MeO—Ph |
| H | H | i-Pr | 3-CF$_3$—Ph |
| H | H | i-Pr | 4-CF$_3$—Ph |
| H | H | i-Pr | Ph |
| 4-F | H | cyclo-Pr | 2-Cl—Ph |
| 4-F | H | cyclo-Pr | 3,4-di-Cl—Ph |
| 4-F | H | cyclo-Pr | 3,5-di-Cl—Ph |
| 4-F | H | cyclo-Pr | 2-Me—Ph |
| 4-F | H | cyclo-Pr | 3-Me—Ph |
| 4-F | H | cyclo-Pr | 4-F—Ph |
| 4-F | H | cyclo-Pr | 3-MeO—Ph |
| 4-F | H | cyclo-Pr | 3,4-di-MeO—Ph |
| 4-F | H | cyclo-Pr | 3,5-di-MeO—Ph |
| 4-F | H | cyclo-Pr | 3,4,5-tri-MeO—Ph |
| 4-F | H | cyclo-Pr | 4-OH—Ph |
| 4-F | H | cyclo-Pr | 4-NMe$_2$—Ph |
| 4-F | H | cyclo-Pr | 4-CF$_3$—Ph |
| H | H | cyclo-Pr | Ph |
| H | H | cyclo-Pr | 3-Cl—Ph |
| H | H | cyclo-Pr | 4-Cl—Ph |
| H | H | cyclo-Pr | 3-Me—Ph |
| H | H | cyclo-Pr | 4-Me—Ph |
| H | H | cyclo-Pr | 3-MeO—Ph |
| H | H | cyclo-Pr | 4-MeO—Ph |
| H | H | cyclo-Pr | 3-CF$_3$—Ph |
| H | H | cyclo-Pr | 4-CF$_3$—Ph |
| H | H | cyclo-Pr | 3,4-di-MeO—Ph |
| H | H | cyclo-Pr | PhCH$_2$ |
| H | H | cyclo-Pr | 4-Ph—Ph |
| 4-Cl | H | cyclo-Pr | 3-Cl—Ph |
| 4-Cl | H | cyclo-Pr | 3-Me—Ph |
| 4-Cl | H | cyclo-Pr | 4-CF$_3$—Ph |
| 4-Cl | H | cyclo-Pr | 3-MeO—Ph |
| 4-Cl | H | cyclo-Pr | 3,4-di-MeO—Ph |
| 4-Cl | H | cyclo-Pr | PhCH$_2$ |

Further, pharmaceutically acceptable salts such as potassium salts or esters such as ethyl esters or methyl esters of these compounds can be prepared in the same manner.

The compounds of the present invention exhibit high inhibitory activities against the cholesterol biosynthesis wherein HMG-CoA reductase acts as a rate limiting enzyme, as shown by the test results given hereinafter, and thus are capable of suppressing or reducing the amount of cholesterol in blood as lipoprotein. Thus, the compounds of the present invention are useful as curing agents against hyperlipidemia, hyperlipoproteinemia and atheroscleosis.

They may be formulated into various suitable formulations depending upon the manner of the administration. The compounds of the present invention may be administered in the form of free acids or in the form of physiologically hydrolyzable and acceptable esters or lactones, or pharmaceutically acceptable salts.

The pharmaceutical composition of the present invention is preferably administered orally in the form of the compound of the present invention per se or in the form of powders, granules, tablets or capsules formulated by mixing the compound of the present invention with a suitable pharmaceutically acceptable carrier including a binder such as hydroxypropyl cellulose, syrup, gum arabic, gelatin, sorbitol, tragacanth gum, polyvinyl pyrrolidone or CMC-Ca, an excipient such as lactose, sugar, corn starch, calcium phosphate, sorbitol, glycine or crystal cellulose powder, a lubricant such as magnesium stearate, talk, polyethylene glycol or silica, and a disintegrator such as potato starch.

However, the pharmaceutical composition of the present invention is not limited to such oral administration and it is applicable for parenteral administration. For example, it may be administered in the form of e.g. a suppository formulated by using oily base material such as cacao butter, polyethylene glycol, lanolin or fatty acid triglyceride, a transdermal therapeutic base formulated by using liquid paraffin, white vaseline, a higher alcohol, Macrogol ointment, hydrophilic ointment or hydro-gel base material, an injection formulation formulated by using one or more materials selected from the group consisting of polyethylene glycol, hydro-gel base material, distilled water, distilled water for injection and excipient such as lactose or corn starch, or a formulation for administration through mucous membranes such as an ocular mucous membrane, a nasal mucous membrane and an oral mucous membrane.

Further, the compounds of the present invention may be combined with basic ion-exchange resins which are capable of binding bile acids and yet not being absorbed in gastraintestinal tract.

The daily dose of the compound of the formula I is from 0.05 too 500 mg, preferably from 0.5 to 50 mg for an ault. It is administered from once to three times per day. The dose may of course be varied depending upon the age, the the weight or the condition of illness of the patient.

The copounds of the formulas II to VIII are novel, and they are important intermediates for the preparation of the compounds of the formula I. Accordingly, the present invention relates also to the compounds of the formulas II to VIII and the processes for their production.

Now, the present invention will be described in further detail with reference to Test Examples for the pharmacological activities of the compounds of the present invention, their Preparation Examples and Formulation Examples. However, it should be understood that the present invention is by no means restricted by such specific Examples.

PHARMACOLOGICAL TEST EXAMPLES

Test A: Inhibition of cholestoerol biosynthesis from acetate in vitro

Enzyme solution was prepared from liver of male Wistar rat billialy connulated and discharged bile for over 24 hours. Liver was cut out at mid-dark and microsome and supernatant fraction which was precipitable with 40-80% of saturation of ammonium sulfate (sup fraction) were prepared from liver homogenate according to the modified merhod of Knauss et. al.; Kuroda, M., et. al., Biochim. Biophys. Acta, 489, 119 (1977). For assay of cholesterol biosynthesis, microsome (0.1 mg protein) and sup fraction (1.0 mg protein) were incubated for 2 hours at 37° C. in 200 µl of the reaction mixture containing ATP; 1 mM, Glutathione; 6 mM, Glucose-1-phosphate; 10 mM, NAD; 0.25 mM, NADP; 0.25 mM, CoA; 0.04 mM and 0.2 mM [2-$^{14}$C]sodium acetate (0.2 µCi) with 4 µl of test compound solution dissolved in water or dimethyl sulfoxide. To stop reaction and saponify, 1 ml of 15% EtOH-KOH was added to the reactions and heated at 75° C. for 1 hour. Nonsaponifiable lipids were extracted with petroleum ether and incorporated $^{14}$C radioactivity was counted. Inhibitory activity of compounds was indicated with IC50.

Test B: Inhibition of cholesterol biosynthesis in culture cells

Hep G2 cells at over 5th passage were seeded to 12 well plates and incubated with Dulbecco's modified Eagle (DME) medium containing 10% of fetal bovine serum (FBS) at 37° C., 5% $CO_2$ until cells were confluent for about 7 days. Cells were exposed to the DME medium containing 5% of lipoprotein deficient serum (LpDS) prepared by ultracentrifugation method for over 24 hours. Medium was changed to 0.5 ml of fresh 5% LpDS containing DME before assay and 10 µl of test compound solution dissolved in water or DMSO were added. 0.2 µCi of [2-$^{14}$C]sodium acetate (20 µl) was added at 0 hr(B-1) or 4 hrs(B-2) after addition of compounds. After 4 hrs further incubation with [2-$^{14}$C]sodium acetate, medium was removed and cells were washed with phosphate buffered saline(PBS) chilled at 4° C. Cells were scraped with rubber policeman and collected to tubes with PBS and digested with 0.2 ml of 0.5 N KOH at 37° C. Aliquot of digestion was used for protein analysis and remaining was saponified with 1 ml of 15% EtOH-KOH at 75° C. for 1 hour. Nonsaponifiable lipids were extracted with petroleum ether and $^{14}$C radioactivity was counted. Counts were revised by cell protein and indicated with DPM/mg protein. Inhibitory activity of compounds was indicated with IC50.

Test C: Inhibition of cholesterol biosynthesis in vivo

Male Sprague-Dawley rats weighing about 150 g were fed normal Purina chow diet and water ad libitum, and exposed to 12 hours light/12 hours dark lighting pattern (2:00 PM-2:00 AM dark) prior to use for in vivo inhibition test of cholesterol biosynthesis. Animals were separated groups consisting of five rats as to be average mean body weight in each groups. Test compounds at dosage of 0.02-0.2 mg/kg body weight (0.4 ml/100 g body weight) were dissolved in water or suspended or in 0.5% methyl cellulose and orally administered at 2-3 hours before mid-dark (8:00 PM), while cholesterol biosynthesis reaches to maximum in rats. As control, rats were orally administered only water or vehicle. At 90 minutes after sample administration, rats were injected intraperitoneally with 10 µCi of [2-$^{14}$C]sodium acetate at volume of 0.2 ml per one. 2 Hours later, blood samples were obtained and serum were separated immediately. Total lipids were extracted according to the method of Folch et al. and saponified with EtOH-KOH. Nonsaponifiable lipids were extracted with petroleum ether and radio activity incorporated into nonsaponifiable lipids was counted.

Inhibitory activity was indicated as percent decrease of counts in testing groups (DPM/2 ml serum/2 hours) from that in control group.

With respect to the compounds of the present invention, the inhibitory activities against the cholesterol biosynthesis in which HMG-CoA reductase serves as a rate limiting enzyme, were measured by the above Test A and B. The results are shown in Tables 2, 2-2 and 3. Further, the results of the measurements by Test C are also presented.

TABLE 2

| Inhibitory activities by Test A | |
|---|---|
| Compound | IC$_{50}$ (molar concentration) |
| (Compounds of the present | |

TABLE 2-continued

| | Inhibitory activities by Test A |
|---|---|
| Compound | IC$_{50}$ (molar concentration) |
| invention) | |
| I-5-1 | $1.8 \times 10^{-8}$ |
| I-5-2 | $5.0 \times 10^{-6}$ |
| I-5-3 | $1.0 \times 10^{-7}$ |
| (Reference compounds) | |
| Mevinolin | $1.4 \times 10^{-8}$ |
| CS-514 | $1.25 \times 10^{-8}$ |

In Table 2-2, the relative activities are shown based on the activities of CS-514 by Test A being evaluated to be 1.

TABLE 2-2

| | Relative activities by Test A |
|---|---|
| Compound (Compounds of the present invention) | Relative activities |
| I-3-8 | 5.2 |
| I-5-8 | 4.6 |
| I-5-11 | 15.9 |
| I-5-12 | 14.8 |
| I-5-13 | 15.9 |
| I-5-14 | 16.1 |
| I-5-15 | 14.5 |
| I-5-16 | 1.9 |
| I-5-17 | 12.2 |

In Table 3, the relative activities are shown based on the activities of CS-514 by Test B-1 being evaluated to be 1.

Here, CS-514 showed the activities IC$_{50}$ (molar concentration) of $1.4 \times 10^{-6}$.

TABLE 3

| | Relative activities by Test B-1 |
|---|---|
| Compound (Compounds of the present invention) | Relative activities |
| I-1-12 | 41.3 |
| I-1-13 | 41.6 |
| I-1-14 | 72.5 |
| I-5-8 | 36.1 |
| I-5-10 | 36.9 |
| I-5-11 | 28.4 |
| I-5-12 | 46.3 |
| I-5-15 | 58.5 |

Structures of reference compounds:

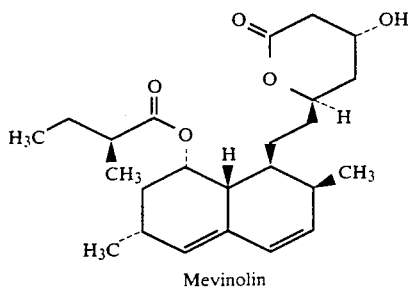

Mevinolin (1)

-continued
Structures of reference compounds:

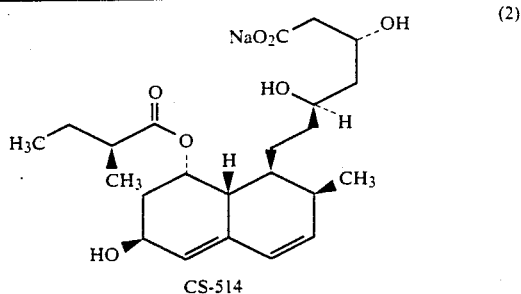

CS-514 (2)

Results of the measurement of the inhibitory activities by Test C

The percent decrease of counts after the oral administration of 0.5 mg/kg of compound I-5-15 was 35% relative to the measured value of the control group. The percent decrease of counts after the oral administration of 10 mg/kg of CS-514 was 55% under the same condition.

The compounds of the present invention exhibited activities superior to the reference compound such as CS-514 or Mevinolin in Test A, and exhibited activities superior to CS-514 in tests B and C.

Test D: Acute toxicity

A 0.5% CMC suspension of a test compound was orally administered to ICR male mice (group of from one to three mice). The acute toxicity was determined based on the mortality after seven days. With compound I-5-8 and I-5-11 of the present invention, the mortality was 0% even when they were orally administered in an amount of 824 mg/kg and 982 mg/kg, respectively.

EXAMPLE 1

Ethyl (E)-3,5-dihydroxy-7-[4'-(4''-fluorophenyl)-6'-methyl-2'-phenylpyrimidin-5'-yl]hept-6-enoate (compound I-1-1)

This compound was prepared by the synthesis comprising the following reaction steps a$_o$ to g.

a$_o$) Ethyl 4-(4'-fluorophenyl)-6-methyl-2-phenyl-pyrimidin-5-yl-carboxylate (VIII-1)

This compound was prepared from p-fluorobenzaldehyde as the starting material via ethyl 2-(4'-fluorobenzylidene)-acetoacetate and ethyl 6-(4'-fluorophenyl)-4-methyl-2-phenyl-1,6-dihydro-5-pyrimidine-carboxylate in accordance with the process disclosed in Japanese Unexamined Patent Publication No. 40272/1986.

a$_o$1) Ethyl 2-(4'-fluorobenzylidene)-acetoacetate (X-1)

8.69 g ($7 \times 10^{-2}$ mol) of p-fluorobenzaldehyde, 9.11 g ($7 \times 10^{-2}$ mol) of ethyl acetoacetate, 0.24 g ($2.8 \times 10^{-3}$ mol) of piperidine and 0.84 g ($1.4 \times 10^{-2}$ mol) of glacial acetic acid were dissolved in 40 ml of dry benzene dehydrated by molecular sieve, and the mixture was refluxed under heating at 100° C. for about 3 hours for azeotropically removing water. After confirming the disappearance of the starting materials by thin layer chromatography, the reaction solution was cooled to room temperature, and 50 ml of ethyl ether was added thereto. The mixture was washed three times with 100 ml of water and twice with 100 ml of a saturated sodium chloride aqueous solution. The ether solution was dried over anhydrous magnesium sulfate, and then the solvent was distilled off under reduced pressure by an evaporator. The residual oil was left to stand overnight in a refrigerator. The solid thereby obtained was recrystallized from hexane to obtain 14.08 g (yield: 85.2%) of slightly yellow prism crystals. Melting point: 80°–82° C.

$a_o2$) Ethyl 6-(4'-fluorophenyl)-4-methyl-2-phenyl-1,6-dihydro-5-pyrimidine-carboxylate (XI-1)

8.42 g ($3.57 \times 10^{-2}$ mol) of compound X-1 and 6.71 g ($4.28 \times 10$ mol) of hydrochloric acid benzamidine were dissolved in 100 ml of n-butanol. Then, 9.74 g ($9.64 \times 10^{-2}$ mol) of triethylamine was added thereto, and the mixture was stirred at 120° C. for about 1.5 hours. After confirming the disappearance of the starting material X-1 by thin layer chromatography, the reaction solution was cooled to room temperature. Then, 100 ml of ethyl acetate was added, and the mixture was washed three times with 100 ml of water. Then, 3% dilute hydrochloric acid was added until the aqueous layer became pH 2, followed by washing and liquid separation. The organic layer was washed with 100 ml of water, and then a saturated sodium bicarbonate aqueous solution was added until the aqueous phase became pH 8, followed by washing and liquid separation. The organic layer was washed with a saturated sodium chloride aqueous solution and dried over anhydrous magnesium sulfate. The solvent was completely distilled off by using an evaporator and then a vacuum pump to obtain 10.26 g (yield: 85.0%) of the product as slightly brown oily substance.

$a_o3$) Ethyl 4-(4'-fluorophenyl)-6-methyl-2-phenyl-pyrimidin-5-yl-carboxylate (VIII-1)

10.26 g ($3.04 \times 10^{-2}$ mol) of compound XI-1 was dissolved in 100 ml of acetone, and the solution was thoroughly stirred under cooling with ice. Then, 7.21 g ($4.56 \times 10^{-2}$ mol) of potassium permanganate powder was gradually added, and the mixture was further stirred at room temperature for 6 hours. After confirming the disappearance of the starting material XI 1 by thin layer chromatography, the product was filtered. The solid remaining on the filter was thoroughly washed with acetone, and the acetone washing solution was combined with the acetone solution, followed by decolorling by activated charcoal treatment. The solvent was distilled off by an evaporator, and the yellow solid thereby obtained was purified by silica gel column chromatography (eluent: 50% ethyl acetate/benzene) to obtain a crude product. The crude product was recrystallized from n-heptane to obtain 3.31 g (yield: 32.4%) of compound VIII-1 as colorless powder. Melting point: 79.5°–81.5° C.

a) 4-(4'-fluorophenyl)-5-hydroxymethyl-6-methyl-2-phenylpyrimidine (VII-1)

3.31 g ($9.85 \times 10^{-3}$ mol) of compound VIII-1 was dissolved in 45 ml of dry toluene dehydrated by molecular sieve, and the solution was cooled to $-10°$ C. under a nitrogen atmosphere and stirred. To this solution, 29.6 ml of a 16 wt % diisobutyl aluminum hydride-toluene solution was gradually dropwise added, and the mixture was stirred at $-10°$ C. for further 1.5 hours. After confirming the complete disappearance of the starting materials by thin layer chromatography, 100 ml of ethyl ether was added to the reaction solution, and dilute hydrochloric acid cooled with ice was gradually dropwise added with due care to terminate the reaction. The ether layer was separated, washed twice with a saturated sodium chloride aqueous solution and dried over anhydrous magnesium sulfate, followed by filtration. The solvent was distilled off by an evaporator and a vacuum pump to obtain 2.62 g (yield: 90.5%) of the product as colorless powder.

b) 4-(4'-fluorophenyl)-6-methyl-2-phenylpyrimidin-5-yl-carboxyaldehyde (VI-1)

2.62 g ($8.9 \times 10^{-3}$ mol) of compound VII-1 was dissolved in 20 ml of dry dichloromethane dehydrated by molecular sieve, and 0.15 g of anhydrous sodium acetate was added and suspended thereto. While stirring the mixture under cooling with ice, 2.88 g ($1.34 \times 10^{-2}$ mol) of a powder of pyridinium chlorochromate was gradually added under stirring and cooling with ice, and the mixture was stirred at room temperature for further about 5 hours. After confirming the disappearance of the starting materials by thin layer chromatography, 100 ml of ethyl ether was added thereto. The reaction mixture was subjected to suction filtration through a silica gel layer. The residual tar was thoroughly washed with ethyl ether until it became powdery, followed by filtration through a silica gel layer, and the filtrate was combined to the previous filtrate. The solvent was distilled off by an evaporator, and the residue was subjected to activated charcoal treatment in the form of a benzene solution. The solvent was distilled off, and the crude crystals thereby obtained were recrystallized from benzene/hexane to obtain 1.40 g (yield: 53.9%) of the product as colorless powder. Melting point: 176°–176.5° C. Further, from the recrystallized mother liquor, 0.98 g (yield: 37.7%) of a slightly impure desired compound was obtained.

c) Ethyl (E)-3-[4'-(4''-fluorophenyl)-6'-methyl-2'-phenylpyrimidin-5'-yl]propenoate (V-1)

0.27 g of 55 wt % sodium hydride was washed with dry hexane, dried under a nitrogen stream and then suspended in 7.5 ml of dry tetrahydrofuran. Under a nitrogen stream, 0.2 g of ethyl diethylphosphonoacetate was added thereto at a temperature of from 20° to 25° C. And the mixture was cooled to $-20°$ to $-15°$ C. and stirred. While paying a due attention to heat generation, 1.15 g of ethyl diethylphosphonoacetate was dropwise added (total amount: 1.35 g, $6 \times 10^{-3}$ mol), and the mixture was stirred at $-20°$ to $-15°$ C. for one hour. To this solution, a solution obtained by dissolving 1.46 g ($5 \times 10^{-3}$ mol) of compound VI-1 in 24 ml of dry tetrahydrofuran was dropwise added, and the mixture was returned to room temperature. Then, 10 ml of anhydrous tetrahydrofuran was further added thereto, and the mixture was stirred at room temperature overnight. The reaction solution was poured into ice water and extracted with chloroform. The extract was washed with a saturated sodium chloride aqueous solution and dried over anhydrous magnesium sulfate. After filtration, the solvent was distilled off to obtain 1.70 g (yield: 93.9%) of the product as colorless powder. Melting point: 91°–97° C.

d) 3-[4'-(4''-fluorophenyl)-6'-methyl-2'-phenylpyrimidin-5'-yl-]prop-2-en-1-ol (IV-1)

1.70 g ($4.7 \times 10^{-3}$ mol) of compound V-1 was dissolved in 45 ml of dry tetrahydrofuran, and the mixture was stirred under a nitrogen stream at 0° C. To this solution, 14.1 ml of a 16 wt % diisobutyl aluminum hydride toluene solution was dropwise added, and the mixture was further stirred at 0° C. for 1.5 hours. After confirming the complete disappearance of the starting material V-1 by thin layer chromatography, a saturated sodium sulfate aqueous solution was added at 0° C. to terminate the reaction. Ethyl ether was added to the reaction mixture, and then dilute hydrochloric acid was added thereto to bring the pH to 2. Then, the ether layer was separated and washed with a saturated sodium chloride aqueous solution until the layer became neutral. Then, it was dried over anhydrous magnesium sulfate and then filtered. The solvent was distilled off to obtain 1.44 g (yield: 95.7%) of the product as slightly yellow oily substance.

e) (E)-3-[4'-(4''-fluorophenyl) 6'-methyl-2'-phenyl-pyrimidin-5'-yl]prop-2-enal (III-1)

1.44 g ($4.5 \times 10^{-3}$ mol) of compound IV-1 was dissolved in 35 ml of dry tetrahydrofuran. To this solution, 4 g of a powder of activated manganese dioxide was added, and the mixture was thoroughly stirred at room temperature. Three hours later, 3.8 g of activated manganese dioxide was further added thereto, the mixture as stirred at room temperature for 4.5 hours. After confirming the disappearance of the starting material by thin layer chromatography, the reaction mixture was filtered through sellaite. The sellaite was thoroughly washed with dry tetrahydrofuran, and the washing solution was combined to the previous filtrate. The solvent was distilled off by an evaporator, and the residue was purified by silica gel column chromatography (eluent: benzene/ethyl acetate) to obtain 0.85 g (yield: 59.4%) of the product as slightly yellow powder. Melting point: 128°-132° C.

f) Ethyl (E)-7-[4'-(4''-fluorophenyl)-6'-methyl-2'-phenylpyrimidin-5'-yl]-5-hydroxy-3-oxohept 6-enoate (II-1)

0.20 g of 55 wt % sodium hydride was washed with dry hexane, dried under a nitrogen stream and suspended in 55 ml of dry tetrahydrofuran. Under a nitrogen stream, the suspension was stirred at −15° C. and 0.59 g ($4.54 \times 10^{-3}$ mo) of ethyl acetoacetate was gradually dropwise added thereto. After stirring the mixture at −15° C. for 20 minutes, 2.64 ml ($4.49 \times 10^{-3}$ mol) of a 1.7 mol/liter n-butyllithium-n-hexane solution was dropwise added thereto, and the mixture was further stirred at 20° C. Then, a solution obtained by dissolving 0.85 g ($2.67 \times 10^{-3}$ mol) of compound III-1 in 15 ml of dry tetrahydrofuran, was dropwise added thereto, and the mixture was stirred for 3.5 hours. To the reaction mixture, hydrochloric acid cooled with ice was added to terminate the reaction. The reaction mixture was extracted with ethyl ether. The ether layer was washed with water and a saturated sodium chloride aqueous solution, dried over anhydrous magnesium sulfate and filtered. The solvent was distilled off by an evaporator, and the residue was purified by silica gel chromatography (eluent: benzene/ethyl acetate) to obtain 0.27 g (yield: 22.6%) of the product as slightly brown waxy substance. Melting point: 68°-78° C.

g) Ethyl (E)-3,5-dihydroxy-7-[4'-(4''-fluorophenyl)-6'-methyl-2'-phenylpyrimidin-5'-yl]hept-6-enoate (I-1-1)

0.23 g ($5.13 \times 10^{-4}$ mol) of compound II 1 was dissolved in 3 ml of ethanol, and the solution was cooled to 0° C. Then, 21 mg ($5.64 \times 10^{-4}$ mol) of sodium borohydride was added thereto, and the mixture was stirred for 8 hours. Then, 10 ml of ethyl ether was added thereto under cooling with ice, and the reaction was terminated by an addition of 6N-hydrochloric acid. The pH of the solution was adjusted to 2, and the ethyl ether layer was separated and washed with water until the washing solution became neutral. After washing with a saturated sodium chloride aqueous solution, the ether layer was dried over anhydrous magnesium sulfate and filtered. The solvent was distilled off by an evaporator, and the residue was purified by silica gel chromatography (eluent: benzene/ethyl acetate) to obtain 0.10 g (yield: 43.3%) of the product as slightly yellow waxy substance. Melting point: 58°-73° C.

h) Sodium salt of (E)-3,5-dihydroxy-7-[4'-(4''-fluorophenyl)-6'methyl-2 2'-phenylpyrimidin-5'-yl]hept-6-enoic acid (I-5-1: sodium salt of I-1-1)

94.3 mg ($2.1 \times 10^{-4}$ mol) of I-1-1 was dissolved in 6 ml of ethanol. Then, 0.38 ml of a 0.5N sodium hydroxide aqueous solution was dropwise added thereto. The mixture was stirred at room temperature for 2 hours. Ethanol was distilled off at 45° C. under reduced pressure, and 5 ml of distilled water was added thereto. The remaining starting material was extracted with ethyl ether. The aqueous layer was freeze-dried to obtain 91.5 mg (yield: 98.1%) of a hygroscopic colorless powder. Melting point: 82°-94° C.

In the same manner as in Example 1-$a_o$($a_o$-1 to $a_o$-3), compounds VIII-2 to VIII-7 were prepared.

TABLE 4

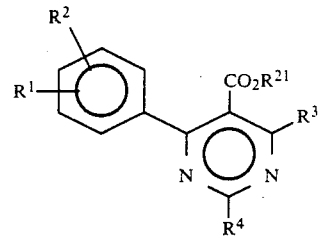

| Compound | R¹ | R² | R³ | R⁴ | R²¹ | m.p. (°C.) |
|---|---|---|---|---|---|---|
| VIII-2 | H | H | Me | Me | Et | Oil |
| NMR (in CDCl₃) δppm: 1.05(t,3H,J=7Hz), 2.58(s,3H), 2.75(s,3H), 4.15(q,2H,J=7Hz), 7.1~7.9(m,5H) | | | | | | |
| VIII-3 | H | H | Me | Ph | Et | Oil |
| NMR (in CDCl₃) δppm: 1.08(t,3H,J=7Hz), 2.65(s,3H), 4.15(q,2H, J=7Hz), 7.1~7.8(m,5H), 8.3~8.6(m,5H) | | | | | | |
| VIII-4 | 4-F | H | Me | 4-Cl—Ph | Et | 105-108.5 |
| VIII-5 | 3-Me | 5-Me | Me | Ph | Et | Oil |
| NMR (in CDCl₃) δppm: 1.10(t,3H,J=7Hz), 2.35(s,6H), 2.64(s,3H), 4.19(q,2H,J=7Hz), 6.9~8.7(m,8H) | | | | | | |
| VIII-6 | 4-R | H | Me | t-Bu | Et | Oil |
| NMR (in CDCl₃) δppm: 1.12(t,3H,J=7Hz), 1.41(s,9H), 2.56(s,3H), 4.20(q,2H,J=7Hz), 6.9~7.8(m,4H) | | | | | | |
| VIII-7 | 4-Br | H | Me | Ph | Et | Oil |
| NMR (in CDCl₃) δppm: 1.10(t,3H,J=7Hz), 2.60(s,3H), 4.12(s,2H, J=7Hz), 7.0~8.7(m,9H) | | | | | | |

Compound VIII-8 was prepared by the process of the following Example 2-a$_o$(a$_o$-1 to a$_o$-3).

EXAMPLE 2-a$_o$)

Ethyl 4-(4'-fluorophenyl)-6-(1'-methylethyl)-2-phenylpyrimidin-5-yl-carboxylate (VIII-8)

This compound was prepared from p-fluorobenzaldehyde as the starting material via methyl 2-(4'-fluorobenzylidene)-isobutyrylacetate and ethyl 6-(4'-fluorophenyl)-4-(1'-methylethyl) 2-phenyl-1,6-dihydro-5-pyrimidin-carboxylate in accordance with the process disclosed in Japanese Unexamined Patent Publication No. 73572/1984.

a$_o$-1) Ethyl 2-(4'-fluorobenzylidene)-isobutyrylacetate (X-2)

This compound was prepared in the same manner as in Example 1-a$_o$-1).

NMR (in CDC$_3$) δ ppm: 1.10(t, 3H, J=7Hz), 1.25(d, 6H, J=7Hz), 2.65 (Heptaplet, 1H, J=7Hz), 4.26(q, 2H, J=7Hz), 7.2~7.9(m, 6H).

a$_o$-2) Ethyl 6-(4'-fluorophenyl)-4-(1'-methylethyl)-2-phenyl-1,6-dihydro-5-pyrimidin-carboxylate (XI-2)

14.79 g (5.6×10$^{-2}$ mol) of compound of X-2 and 13.16 g (8.4×10$^{-2}$ mol) of benzamidine hydrochloride were dissolved in 200 ml of dry ethanol dehydrated by molecular sieve. Then 5.51 g (6.7×10$^{-2}$ mol) of anhydrous sodium acetate was added thereto, and the mixture was stirred at 80° C. for 2 days. After confirming the disappearance of the starting material X-2 by thin layer chromatography, the reaction solution was evaporated by an evaporator to distill off the solvent to dryness. The residue was extracted with ethyl acetate, and the insoluble crystals were removed by filtration. The solvent was distilled off by an evaporator, and the residual oil was dissolved in chloroform. The solution was carefully washed with saturated sodium bicarbonate aqueous solution. Then, the organic layer was washed with a saturated sodium chloride aqueous solution and dried over anhydrous magnesium sulfate. Then, the solvent was completely distilled off by an evaporator and further, by means of a vacuum pump to obtain 19.63 g (yield: 95.8%) of the product as slightly brown oily substance. MS(m/e): 366 (m+)

a$_o$-3) Ethyl 4-(4'-fluorophenyl)-6-(1'-methylethyl)2-phenylpyrimidin-5-yl-carboxylate (VIII-8)

This compound was prepared from compound XI-2 in the same manner as in Example 1-a$_o$-3.

NMR (in CDCl$_3$) δ ppm: 1.09(t, 3H, J=7Hz), 1.37(d, 6H, J=6Hz), 3.20 Heptaplet, 1H, J=6Hz), 4.13(q, 2H, J=7Hz), 6.8~8.7(m, 9H).

Compounds VIII-9 to VIII-17 were prepared in the same manner as in Example 2-a$_o$(a$_o$-1 to a$_o$-3).

TABLE 5

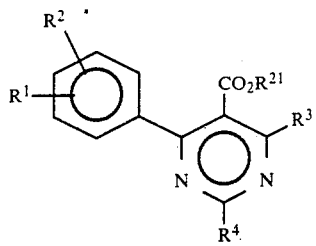

| Compound | R$^1$ | R$^2$ | R$^3$ | R$^4$ | R$^{21}$ | m.p. (°C.) |
|---|---|---|---|---|---|---|
| VIII-9 | 4-F | H | n-Pr | Ph | Et | Oil |
| | NMR (in CDCl$_3$) δppm: 1.05(t,3H,J=7Hz), 1.10(t,3H,J=7Hz), 1.5~2.1(m,2H), 2.7~3.1(t,2H,J=8Hz), 4.18 (q,2H,J=7Hz), 6.7~8.9(m,9H) | | | | | |
| VIII-10 | 4-F | H | i-Pr | 4-Me—Ph | Et | Oil |
| | NMR (in CDCl$_3$) δppm: 1.10(t,3H,J=7Hz), 1.37(d,6H,J=7Hz), 2.35 (s,3H), 3.20(Heptaplet,1H,J=7Hz), 4.14(q, 2H,J=7Hz), 6.9~8.4(m,8H) | | | | | |
| VIII-11 | 4-F | H | cyclo-Pr | Ph | Me | Oil |
| | NMR (in CDCl$_3$) δppm: 0.8~2.5(m,5H), 3.70(s,3H), 6.8~8.8(m, 9H) | | | | | |
| VIII-12 | 4-F | H | cyclo-Pr | CH$_2$Ph | Me | Oil |
| | NMR (in CDCl$_3$) δppm: 0.7~1.6(m,4H), 1.8~2.4(m,1H), 3.6(s,3H), 4.15(s,2H), 6.7~7.8(m,9H) | | | | | |
| VIII-13 | 4-F | H | cyclo-Pr | 3-Cl—Ph | Me | 112–115 |
| VIII-14 | 4-F | H | cyclo-Pr | 4-MeO—Ph | Me | 88–94 |
| VIII-15 | 4-F | H | cyclo-Pr | 4-Me—Ph | Me | 99–102 |
| VIII-16 | 4-F | H | cyclo-Pr | 4-Ph—Ph | Me | 127–131 |
| VIII-17 | 4-F | H | cyclo-Pr | 3-CF$_3$—Ph | Me | 107–109 |

Compounds VII-2 to VII-17 were prepared in the same manner as in Example 1-a.

TABLE 6

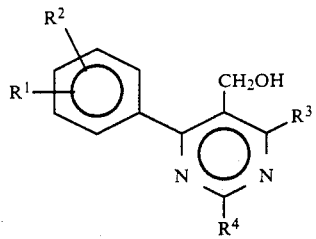

| Compound | R$^1$ | R$^2$ | R$^3$ | R$^4$ | m.p. (°C.) |
|---|---|---|---|---|---|
| VII-2 | H | H | Me | Me | 147–150 |
| VII-3 | H | H | Me | Ph | 169–170.5 |
| VII-4 | 4-F | H | Me | 4-Cl—Ph | 160–160.5 |
| VII-5 | 3-Me | 5-Me | Me | Ph | 114–117 |
| VII-6 | 4-F | H | Me | t-Bu | 137–139 |
| VII-7 | 4-Br | H | Me | Ph | 163–171 |
| VII-8 | 4-F | H | i-Pr | Ph | 191–192 |
| VII-9 | 4-F | H | n-Pr | Ph | 153–157 |
| VII-10 | 4-F | H | i-Pr | 4-Me—Ph | 188–189 |
| VII-11 | 4-F | H | cyclo-Pr | Ph | 190–192 |
| VII-12 | 4-F | H | cyclo-Pr | CH$_2$Ph | <30 |
| VII-13 | 4-F | H | cyclo-Pr | 3-Cl—Ph | 165–172 |
| VII-14 | 4-F | H | cyclo-Pr | 4-MeO—Ph | 173–174 |
| VII-15 | 4-F | H | cyclo-Pr | 4-Me—Ph | 194–195 |
| VII-16 | 4-F | H | cyclo-Pr | 4-Ph—Ph | 212–213 |
| VII-17 | 4-F | H | cyclo-Pr | 3-CF$_3$—Ph | 166–167 |

Compounds VI-2 to VI-17 were prepared in the same manner as in Example I-b.

TABLE 7

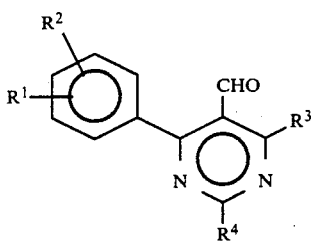

| Compound | R¹ | R² | R³ | R⁴ | m.p. (°C.) |
|---|---|---|---|---|---|
| VI-2 | H | H | Me | Me | 87-88 |
| NMR (in CDCl₃)δppm: | | | | | |
| 2.8(broad s,6H), 7.2~7.8(m,5H), 10.05 | | | | | |
| (s,1H) | | | | | |
| VI-3 | H | H | Me | Ph | 130-132 |
| VI-4 | 4-F | H | Me | 4-Cl-Ph | 163-164 |
| VI-5 | 3-Me | 5-Me | Me | Ph | 127-128 |
| VI-6 | 4-F | H | Me | t-Bu | 68-71 |
| VI-7 | 4-Br | H | Me | Ph | 166-173 |
| VI-8 | 4-F | H | i-Pr | Ph | 129-133 |
| VI-9 | 4-F | H | n-Pr | Ph | 98-101 |
| VI-10 | 4-F | H | i-Pr | 4-Me-Ph | 129-130 |
| VI-11 | 4-F | H | cyclo-Pr | Ph | 147-148 |
| VI-12 | 4-F | H | cyclo-Pr | CH₂Ph | 79-82 |
| VI-13 | 4-F | H | cyclo-Pr | 3-Cl-Ph | 125-128 |
| VI-14 | 4-F | H | cyclo-Pr | 4-MeO-Ph | 132-136 |
| VI-15 | 4-F | H | cyclo-Pr | 4-Me-Ph | 160-162 |
| VI-16 | 4-F | H | cyclo-Pr | 4-Ph-Ph | 177-178 |
| VI-17 | 4-F | H | cyclo-Pr | 3-CF₃-Ph | 130-133 |

Compounds V-2 to V-9 were prepared in the same manner as in Example 1-c.

TABLE 8

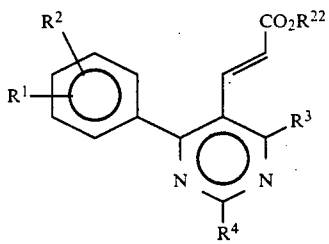

| Compound | R¹ | R² | R³ | R⁴ | R²² | m.p. (°C.) |
|---|---|---|---|---|---|---|
| V-2 | H | H | Me | Me | Et | Oil |
| NMR(in CDCl₃) δ ppm: | | | | | | |
| 1.23(t, 3H, J=7Hz), 2.58(s, 3H), 2.68(s, 3H), | | | | | | |
| 4.13(q, 2H, J=7Hz), 5.88(d, 1H, J=16Hz), | | | | | | |
| 7.2~7.8(m, 6H) | | | | | | |
| V-3 | H | H | Me | Ph | Et | 108-108.5 |
| V-4 | 4-F | H | Me | 4-Cl-Ph | Et | 91-97 |
| V-5 | 3-Me | 5-Me | Me | Ph | Et | 102-104 |
| V-6 | 4-F | H | Me | t-Bu | Et | Oil |
| NMR(in CDCl₃) δ ppm: | | | | | | |
| 1.28(t, 3H, J=7Hz), 1.41(s, 9H), 2.60(s, 3H), | | | | | | |
| 4.15(q, 2H, J=7Hz), 5.93(d, 1H, J=16Hz), | | | | | | |
| 6.8~7.8(m, 5H) | | | | | | |
| V-7 | 4-Br | H | Me | Ph | Et | 147-155 |
| V-8 | 4-F | H | i-Pr | Ph | Et | 94-101 |
| V-9 | 4-F | H | n-Pr | Ph | Et | 82-90 |

Compounds IV-2 to IV-9 were prepared in the same manner as in Example 1-d.

TABLE 9

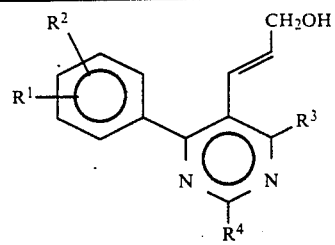

| Compound | R¹ | R² | R³ | R⁴ | m.p. (°C.) |
|---|---|---|---|---|---|
| IV-2 | H | H | Me | Me | Oil |
| IV-3 | H | H | Me | Ph | Oil |
| IV-4 | 4-F | H | Me | 4-Cl-Ph | 130-134 |
| IV-5 | 3-Me | 5-Me | Me | Ph | 109-113 |
| IV-6 | 4-F | H | Me | t-Bu | Oil |
| NMR(in CDCl₃) δ ppm: | | | | | |
| 1.40(s, 9H), 2.52(s, 3H), 4.0~4.3(m, 2H), | | | | | |
| 5.5~6.0(m, 1H), 6.45(d, 1H, J=17Hz), | | | | | |
| 6.8~7.9(m, 4H) | | | | | |
| IV-7 | 4-Br | H | Me | Ph | 105-111 |
| IV-8 | 4-F | H | i-Pr | Ph | 94-101 |
| IV-9 | 4-F | H | n-Pr | Ph | 82-90 |

Compounds III-2 to III-9 were prepared in the same manner as in Example I-e.

TABLE 10

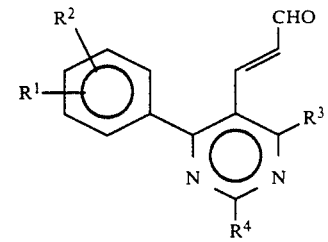

| Compound | R¹ | R² | R³ | R⁴ | m.p. (°C.) |
|---|---|---|---|---|---|
| III-2 | H | H | Me | Me | Oil |
| NMR(in CDCl₃) δ ppm: | | | | | |
| 2.63(s, 3H,), 2.73(s, 3H), 6.20(d, d, 1H, J=7Hz, | | | | | |
| 16Hz), 7.2~7.7(m, 6H), 9.38(d, 1H, J=7Hz) | | | | | |
| III-3 | H | H | Me | Ph | 144-145 |
| III-4 | 4-F | H | Me | 4-Cl-Ph | 161-163 |
| III-5 | 3-Me | 5-Me | Me | Ph | 159-161 |
| III-6 | 4-F | H | Me | t-Bu | Oil |
| NMR(in CDCl₃) δ ppm: | | | | | |
| 1.40(s, 9H), 2.62(s, 3H), 6.23(d, d, 1H, J=7, | | | | | |
| 16Hz), 6.8~7.7(m, 5H), 9.43(d, 1H, J=7Hz) | | | | | |
| III-7 | 4-Br | H | Me | Ph | 150-154 |
| III-8 | 4-F | H | i-Pr | Ph | 141-143 |
| III-9 | 4-F | H | n-Pr | Ph | 125-128 |

Compound III-10 was prepared by a process of the following Example 3 (3-1, 3-m).

EXAMPLE 3-1

5-(3'-ethoxy-1'-hydroxy-2'-propenyl)-4-(4'-fluorophenyl)6-(1'-methylethyl)-2-(4'-methylphenyl)pyrimidine (compound IX-10)

6.65 g (18.4 mmol) of cis-1-ethoxy-2-(tri-n-butylstannyl)ethylene was dissolved in 180 ml of dry tetrahydrofuran, and the solution was cooled to −78° C. under a nitrogen stream. To this solution, 13.2 ml (20 mmol) of a 15 wt % n-butyllithium-n-hexane solution was dropwise added, and the mixture was stirred for 45 minutes. Then, a solution obtained by dissolving 3.08 g (9.2 mmol) of compound VI-10 in 180 ml of dry tetrahydrofuran was dropwise added thereto. The reaction mixture was stirred at −78° C. for 1.5 hours, and then 5 ml of a saturated ammonium chloride aqueous solution was added to terminate the reaction. The organic layer was extracted with diethyl ether, and the ether extract was washed with a saturated sodium chloride aqueous solution and dried over anhydrous magnesium sulfate. The solvent was distilled off under reduced pressure, and the residue was subjected to liquid separation between hexane and acetonitrile. The acetonitrile layer was subjected to distillation under reduced pressure to remove the solvent and to obtain the desired product as slightly yellow powder. Melting point: 108°–118° C.

Compounds IX-11 to IX-17 were prepared in the same manner as in Example 3-1.

TABLE 11

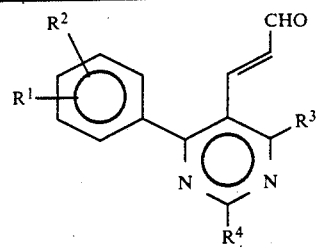

| Compound | $R^1$ | $R^2$ | $R^3$ | $R^4$ | m.p. (°C.) |
|---|---|---|---|---|---|
| IX-11 | 4-F | H | cyclo-Pr | Ph | 138–145 |
| IX-12 | 4-F | H | cyclo-Pr | $CH_2Ph$ | 155–158 |
| IX-13 | 4-F | H | cyclo-Pr | 3-Cl—Ph | 35–38 |
| IX-14 | 4-F | H | cyclo-Pr | 4-MeO—Ph | 142–144 |
| IX-15 | 4-F | H | cyclo-Pr | 4-Me—Ph | 152–155 |
| IX-16 | 4-F | H | cyclo-Pr | 4-Ph—Ph | 102–105 |
| IX-17 | 4-F | H | cyclo-Pr | 3-$CF_3$—Ph | 30–40 |

EXAMPLE 3-m (E)-3-[4'-(4''-fluorophenyl)-6'-(1'-methylethyl)-2'-(4''-methylphenyl)pyrimidin-5'-yl]prop-2-enal (compound III-10)

3.52 g of compound IX-10 was dissolved in 75 ml of tetrahydrofuran, and 14 ml of water and 200 mg of p-toluene sulfonic acid were added thereto. The mixture was stirred at room temperature for 5 hours. The reaction solution was extracted a few times with diethyl ether, and the ether layer was washed with a saturated sodium chloride auqeous solution and dried over anhydrous magnesium sulfate. Then, solvent was distilled off under reduced pressure. The residue was purified by silica gel column chromatography (eluent: 50% ethyl acetate/benzene) to obtain the desired product as slightly yellow powder. Melting point: 129°–131° C.

Compounds III-11 to III-17 were prepared in the same manner as in Example 3-m.

TABLE 12

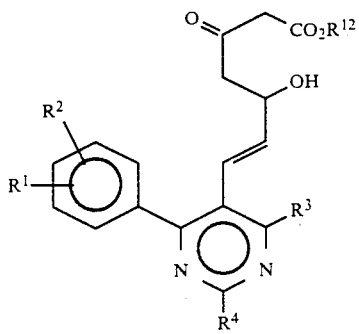

| Compound | $R^1$ | $R^2$ | $R^3$ | $R^4$ | m.p. (°C.) |
|---|---|---|---|---|---|
| III-11 | 4-F | H | cyclo-Pr | Ph | 173–174 |
| III-12 | 4-F | H | cyclo-Pr | $CH_2Ph$ | 176–178 |
| III-13 | 4-F | H | cyclo-Pr | 3-Cl—Ph | 146–152 |
| III-14 | 4-F | H | cyclo-Pr | 4-MeO—Ph | 135–143 |
| III-15 | 4-F | H | cyclo-Pr | 4-Me—Ph | 171–173 |
| III-16 | 4-F | H | cyclo-Pr | 4-Ph—Ph | 209–211 |
| III-17 | 4-F | H | cyclo-Pr | 3-$CF_3$—Ph | 146–148 |

Compounds II-2 to II-17 were prepared in the same manner as in Example I-f.

TABLE 13

| Compound | $R^1$ | $R^2$ | $R^3$ | $R^4$ | $R^{12}$ | m.p. (°C.) |
|---|---|---|---|---|---|---|
| II-2 | H | H | Me | Me | Et | Oil |
| MS(m/e): 368($M^+$) 350, 209 | | | | | | |
| II-3 | H | H | Me | Ph | Et | Oil |
| MS(m/e): 416($M^+$) 398, 340, 271 | | | | | | |
| II-4 | 4-F | H | Me | 4-Cl—Ph | Et | 62–63 |
| II-5 | 3-Me | 5-Me | Me | Ph | Et | Oil |
| MS(m/e): 440($M^+$ − $H_2O$), 299, 258 | | | | | | |
| II-6 | 4-F | H | Me | t-Bu | Et | Oil |
| MS(m/e): 428($M^+$), 410($M^+$ − $H_2O$), 283, 256 | | | | | | |
| II-7 | 4-Br | H | Me | Ph | Et | 112–115 |
| II-8 | 4-F | H | i-Pr | Ph | Et | 115–120 |
| II-9 | 4-F | H | n-Pr | Ph | Et | Oil |
| MS(m/e): 477($M^+$ + H), 458($M^+$ − $H_2O$), 349, 317 | | | | | | |
| II-10 | 4-F | H | i-Pr | 4-Me—Ph | Et | 103–104 |
| II-11 | 4-F | H | cyclo-Pr | Ph | Et | 96–101 |
| II-12 | 4-F | H | cyclo-Pr | $CH_2Ph$ | Et | Oil |
| NMR(in $CDCl_3$) δ ppm: 0.6∼1.4(m, 4H), 1.20(t, 3H, J=7Hz), 1.9∼2.4 (m, 1H), 2.5∼2.7(m, 2H), 3.0∼3.5(m, 1H), 3.33(s, 2H), 4.08(q, 2H, J=7Hz), 4.10(s, 2H), 4.3∼4.7(m, 1H), 5.53(d, d, 1H, J=6Hz, 16Hz), 6.50(d, 1H, J=16Hz), 6.7∼7.6(m, 9H) | | | | | | |
| II-13 | 4-F | H | cyclo-Pr | 3-Cl—Ph | Et | 106–107 |
| II-14 | 4-F | H | cyclo-Pr | 4-MeO—Ph | Et | Oil |
| NMR(in $CDCl_3$) δ ppm: 0.7∼1.6(m, 4H), 1.20(t, 3H, J=7Hz), 2.1∼2.5 (m, 1H), 2.5∼2.8(m, 2H), 2.9∼3.4(m, 1H), 3.37(s, 2H), 3.70(s, 3H), 4.10(q, 2H, J=7Hz), 4.3∼4.9(m, 1H), 5.62(d, d, 1H, J=6Hz, 16Hz), 6.53(d, 1H, J=16Hz), 6.7∼8.6(m, 8H) | | | | | | |
| II-15 | 4-F | H | cyclo-Pr | 4-Me—Ph | Et | 83–87 |
| II-16 | 4-F | H | cyclo-Pr | 4-Ph—Ph | Et | 109–110 |
| II-17 | 4-F | H | cyclo-Pr | 3-$CF_3$—Ph | Et | 115–118 |

Compounds I-1-2 to I-1-6 were prepared in the same manner as in Example I-g.

TABLE 14

[Structure: pyrimidine with phenyl bearing R¹, R² substituents; R³, R⁴ on pyrimidine; side chain HO-CH-CH₂-CH(OH)-CH=CH- with CO₂R¹²]

| Compound | R¹ | R² | R³ | R⁴ | R¹² | m.p. (°C.) |
|---|---|---|---|---|---|---|
| I-1-2 | H | H | Me | Me | Et | Oil |

MS(m/e): 370(M⁺), 325, 211, 154

| I-1-3 | H | H | Me | Ph | Et | Oil |

MS(m/e): 432(M⁺), 301, 273, 154
NMR(in CDCl₃) δ ppm:
1.27(t, 3H, J=7Hz), 1.4~1.8(m, 2H), 2.43 (d, 2H, J=7Hz), 2.65(s, 3H), 3.1~3.4(m, 1H), 3.5~3.7(m, 1H), 4.17(q, 2H, J=8Hz), 4.0~4.3(m, 1H), 4.3~4.6(m, 1H), 5.68 (d, d, 1H, J=15Hz, 5Hz), 6.63(d, 1H, J=15Hz), 7.3~8.6 (m, 10H)

| I-1-4 | 4-F | H | Me | 4-Cl—Ph | Et | 45-52 |

MS(m/e): 484(M⁺), 448, 325, 172
NMR(in CDCl₃) δ ppm:
1.29(t, 3H, J=11Hz), 1.5~1.7(m, 2H), 2.4~2.6(m, 2H), 2.66(s, 3H), 3.5~3.9(m, 2H), 4.19(q, 2H, J=7Hz), 4.2~4.3(m, 1H), 4.4~4.6(m, 1H), 5.68(d, d, 1H, J=6Hz, 17Hz), 6.62 (d, 1H, J=17Hz), 7.1~8.5 (m, 8H)

| I-1-5 | 3-Me | 5-Me | Me | Ph | Et | Oil |

MS(m/e): 460(M⁺), 424, 299
NMR(in CDCl₃) δ ppm:
1.28(t, 3H, J=7Hz), 1.5~1.6(m, 2H), 2.36 (s, 6H), 2.4~2.5(m, 2H), 2.67(s, 3H), 3.4~3.5(m, 1H), 3.7~3.8(m, 1H), 4.18(q, 2H, J=7Hz), 4.1~4.3(m, 1H), 4.4~4.5(m, 1H), 5.67(d, d, 1H, J=6Hz, 17Hz), 6.60(d, 1H, J=17Hz), 7.0~8.5 (m, 8H)

| I-1-6 | 4-F | H | Me | t-Bu | Et | Oil |

MS(m/e): 430(M⁺) 281, 271
NMR(in CDCl₃) δ ppm:
1.28(t, 3H, J=7Hz), 1.42(s, 9H), 1.5~1.6 (m, 2H), 2.4~2.6(m, 2H), 2.57(s, 3H), 3.4~3.6(m, 1H), 3.7~3.8(m, 1H), 4.19(q, 2H, J=7Hz), 4.1~4.3(m, 1H), 4.4~4.6(m, 1H), 5.61(d, d, 1H, J=6Hz, 16Hz), 6.58(d, 1H, J=16Hz), 7.0~7.7(m, 4H)

Compounds I-1-7 was prepared by the process of the following Example 4 (4-g).

EXAMPLE 4-g

Ethyl (E)-3,5-dihydroxy-7-[4'-(4''-bromophenyl)-6'-methyl-2'-phenylpyrimidin-5'-yl]hept-6-enoate (compound I-1-7)

500 mg (1×10⁻³ mol) of compound II-7 was dissolved in 25 ml of dry ethyl ether and 3 ml of dry benzene, and the solution was cooled to −70° C. Then, 33 ml (about 5×10⁻³ mol) of an about 0.15 mol/liter zinc borohydride-ethyl ether solution was added thereto, and the mixture was stirred under a nitrogen stream for 4 hours. After confirming the disappearance of the starting material II-7 by thin layer chromatography, 6 ml of methanol and then 12 ml of water were added at −70° C. to terminate the reaction. Then, 120 ml of water and 120 ml of ethyl ether were further added, and the mixture was adjusted to pH4 with a dilute acetic acid aqueous solution. The ether layer was washed with water and then with a saturated sodium chloride aqueous solution and dried over anhydrous magnesium sulfate. Then, the solvent was distilled off by an evaporator, and the residual solid was purified by silica gel column chromatography (eluent: benzene/ethyl acetate) to obtain the desired compound as slightly yellow powder. Melting point: 125.5°-127.5° C.

MS(M/e): 512(M⁺+H) 475, 401, 351. NMR(in CDCl₃) δ pmm: 1.29(t, 3H, J=7Hz), 1.4~1.7(m, 2H), 2.4~2.5(m, 2H), 2.66(s, 3H), 3.5~3.9(m×2, 2H), 4.19(q, 2H, J=7Hz), 4.1~4.3(m, 1H), 4.3~4.6(m, 1H), 5.65(d, d, 1H, J=6Hz, 17 Hz), 6.62(d, 1H, J=17Hz), 7.3~8.6(m, 9H).

Compounds I-1-8 to I-1-17 were prepared in the same manner as in Example 4-g.

TABLE 15

[Structure: pyrimidine with phenyl bearing R¹, R² substituents; R³, R⁴ on pyrimidine; side chain with E-alkene, HO-CH-CH₂-CH(OH)-CH=CH- and CO₂R¹²]

| Compound | R¹ | R² | R³ | R⁴ | R¹² | m.p. (°C.) |
|---|---|---|---|---|---|---|
| I-1-8 | 4-F | H | i-Pr | Ph | Et | 80-88 |

MS(m/e): 478(M⁺) 460, 442, 369, 319, 172
NMR(in CDCl₃) δ ppm:
1.28(t,3H,J=7Hz), 1.35(d,6H,J=7Hz), 1.4~1.7(m,2H), 2.4~2.5(m,2H) 3.44 (Heptaplet, 1H,J=7Hz), 3.5~3.9(m × 2,2H), 4.18(q,2 H,J=7Hz), 4.1~4.3(m,1H), 4.3~4.6(m,1H), 5.51(d.d,1H,J=6Hz,17Hz), 6.69(d,1H,J=17Hz), 7.0~8.7(m,9H)

| I-1-9 | 4-F | H | n-Pr | Ph | Et | 85-89 |

MS(m/e): 478(M⁺) 460, 369, 301
NMR(in CDCl₃) δ ppm:
1.05(t,3H,J=7Hz), 1.29(t,3H,J=7Hz), 1.4~1.7(m,2H), 1.7~2.1(m,2H), 2.4~2.5(m, 2H), 2.90(t,2H,J=8Hz, 3.4~3.6(m,1H), 3.6~3.8(m,1H), 4.19(q,2H,J=7Hz), 4.1~4.3(m,1H), 4.3~4.6(m,1H), 5.56(d,d,1H, J=6Hz,17Hz), 6.68(d,1H,J=17Hz), 7.0~8.7 (m,9H)

| I-1-10 | 4-F | H | i-Pr | 4-Me-Ph | Et | 78-83 |

MS(m/e): 492(M⁺) 456, 333
NMR(in CDCl₃) δ ppm:
1.28(t,3H,J=7Hz), 1.4~1.7(m,2H), 1.35 (d,6H,J=7Hz), 2.4~2.5(m,2H), 2.42(s,3H), 3.44(Heptaplet, H,J=7Hz), 3.4~3.5(m,1H), 3.7~3.8(m,1H), 4.1~4.3(m,1H), 4.19(q, 2H,J=7Hz), 4.3~4.6(m,1H), 5.51(d,d,1H, J=6Hz,17Hz), 6.70(d,1H,J=17Hz), 7.0~8.5 (m,8H)

| I-1-11 | 4-F | H | cyclo-Pr | Ph | Et | 88-90 |

MS(m/e): 476(M⁺), 440, 315
NMR(in CDCl₃) δ ppm:
1.28(t,3H,J=7Hz), 1.0~1.5(m,4H), 1.5~1.9(m,2H), 2.2-2.5(m,1H), 2.4~2.6(m, 2H), 3.5~3.7(m,1H), 3.7~3.9(m,1H), 4.0~4.4(m,1H), 4.19(q,2H,J=7Hz), 4.4~4.7 (m,1H), 5.78(d,d1H,J=6Hz,17Hz), 6.72(d, 1H,J=17Hz), 7.0~8.6 (m,9H)

| I-1-12 | 4-F | H | cyclo-Pr | CH₂Ph | Et | Oil |

MS(m/e): 490(M⁺), 454, 331, 172
NMR (in CDCl₃) δ ppm:
0.8~1.4(m,4H), 1.27(t,3H,J=7Hz), 1.4~1.7 (m,2H), 2.1~2.4(m,1H), 2.4~2.5(m,2H),

TABLE 15-continued

[Structure: pyrimidine with R¹, R² on phenyl; R³, R⁴ on pyrimidine; vinyl-CH(OH)-CH₂-CH(OH)-CH₂-CO₂R¹² side chain]

| Compound | R¹ | R² | R³ | R⁴ | R¹² | m.p. (°C.) |
|---|---|---|---|---|---|---|

3.4~3.9(m,2H), 4.0~4.3(m,1H), 4.17(q,2H, J=7Hz), 4.17(s,2H), 4.3~4.6(m,1H), 5.65 (d,d,1H,J=6Hz,16Hz), 6.60(d,1H,J=16Hz), 6.9-7.7(m,9H)

I-1-13   4-F   H   cyclo-Pr   3-Cl—Ph   Et   129-130
MS(m/e, FAB): 511(M⁺+H), 475, 154
NMR (in CDCl₃) δ ppm:
0.9~1.4(m,4H), 1.29(t,3H,J=7Hz), 1.4~1.8 (m,2H), 2.2~2.5(m,1H), 2.4~2.6(m,2H), 3.2~3.9(m,2H), 4.0~4.4(m,1H), 4.20(q,2H, J=7Hz), 4.4~4.7(m,1H), 5.77(d,d,1H,J=6Hz, 16Hz), 6.75(d,1H,J=16Hz), 7.0~8.5(m,8H)

I-1-14   4-F   H   cyclo-Pr   4-MeO—Ph   Et   30-35
MS(m/e): 506(M⁺), 470, 345, 172
NMR (in CDCl₃) δ ppm:
0.9~1.4(m,4H), 1.28(t,3H,J=7Hz), 1.4~1.8 (m,2H), 2.2~2.5(m,1H), 2.4~2.6(m,2H), 3.4~3.9(m,2H), 3.86(s,3H), 4.0~4.4(m,1H), 4.19(q,2H,J=7Hz), 4.4~4.7(m,1H), 5.74(d,d, 1H,J=6Hz,16Hz), 6.62(d,1H,J=16Hz), 6.8~8.5 (m,8H)

I-1-15   4-F   H   cyclo-Pr   4-Me—Ph   Et   88-90
MS(m/e): 490(M⁺), 454, 329, 172
NMR (in CDCl₃) δ ppm:
0.9~1.4(m,4H), 1.29(t,3H,J=7Hz), 1.4~1.8 (m,2H), 2.2~2.5(m,1H), 2.40(s,3H), 2.4~2.6(m,2H), 3.3~3.8(m,2H), 4.0~4.3 (m,1H), 4.19(q,2H,J=7Hz), 4.3~4.7(m,1H), 5.77(d,d,1H,J=6Hz,16Hz),6.73(d,1H,J=16Hz), 6.9~8.4(m,8H)

I-1-16   4-F   H   cyclo-Pr   4-Ph—Ph   Et   128-132
MS(m/e): 552(M⁺), 516, 444, 391, 172
NMR (in CDCl₃) δ ppm:
0.9~1.4(m,4H), 1.29(t,3H,J=7Hz), 1.4~1.8 (m,2H), 2.2~2.5(m,1H), 2.4~2.6(m,2H), 3.4~3.9(m,2H), 4.0~4.4(m,1H), 4.20(q,2H, J=7Hz), 4.4~4.8(m,1H), 5.77(d,d,1H,J=6Hz, 16Hz), 6.76(d,1H,J=16Hz), 7.0-8.6(m,13H)

I-1-17   4-F   H   cyclo-Pr   3-CF₃—Ph   Et   118-121
MS(m/e):544(M⁺), 526, 508, 383, 172
NMR (in CDCl₃) δ ppm:
0.9~1.4(m,4H), 1.29(t,3H,J=7Hz), 1.4~1.8 (m,2H), 2.2~2.5(m,1H), 2.4~2.6(m,2H), 3.4~3.9(m,2H), 4.0~4.4(m,1H), 4.20(q,2H, J=7Hz), 4.4~4.7(m,1H), 5.77(d,d,1H,J=6Hz, 16Hz), 6.76(d,1H,J=16Hz), 7.0~8.8(m,8H)

Compounds I-5-2 to I-5-17 were prepared in the same manner as in Example I-h.

TABLE 16

I-5

[Structure: pyrimidine with R¹, R² on phenyl; R³, R⁴ on pyrimidine; vinyl-CH(OH)-CH₂-CH(OH)-CH₂-CO₂R¹² side chain]

| Compound | R¹ | R² | R³ | R⁴ | R¹² | m.p. (°C.) |
|---|---|---|---|---|---|---|
| I-5-2 | H | H | Me | Me | Na | 83-85 |

MS(m/e, FAB): 387(M+Na) 207
NMR (in d₆-DMSO) δ ppm:
1.2~1.5(m,2H), 1.8~2.0(m,2H), 2.50(s, 3H), 2.57(s,3H), 3.0~3.4(m,2H) 3.5~3.8 (m,1H), 4.0~4.4(m,1H), 5.63(d,d,1H,J= 7Hz,16Hz), 6.43(d,1H,J=16Hz), 7.2~7.8 (m,5H)

I-5-3   H   H   Me   Ph   Na   75-78
MS(m/e, FAB): 449(M⁺+Na), 426(M⁺) 271, 176
NMR(in d₆-DMSO) δ ppm:
1.2~1.6(m,2H), 2.02(d,2H,J=7Hz), 2.64 (s,3H), 3.0~3.4(m,1H), 3.3~3.6(m,1H), 3.6~3.9(m,1H), 4.1~4.4(m,1H), 5.76(d,d, 1H,J=5Hz,15Hz), 6.53(d,1H,J=15Hz), 7.3~ 8.5(m,10H)

I-5-4   4-F   H   Me   4-Cl—Ph   Na   132-139
MS(m/e, FAB): 501(M⁺+Na), 479(M⁺+H), 413
NMR(in d₆-DMSO) δ ppm:
1.2~1.6(m,2H), 1.8~2.2(m,2H), 2.63 (s,3H), 3.3~4.0(m,3H), 4.1~4.4(m,1H), 5.78(d,d1H,J=7Hz,16Hz), 6.52(d,1H,J=16 Hz), 7.2~8.5(m,8H)

I-5-5   3-Me   5-Me   Me   Ph   Na   128-136
MS(m/e, FAB): 477(M⁺+Na), 455(M⁺+H), 329, 176
NMR(in d₆-DMSO) δ ppm:
1.2~1.6(m,2H), 1.8~2.1(m,2H), 2.34(s, 6H),2.63(s,3H), 3.0~3.4(m,2H), 3.6~ 3.9(m,1H), 4.1~4.4(m,1H), 5.76(d,d,1H,J= 7Hz,16Hz), 6.48(d,1H,J=16Hz), 7.0~8.6 (m,8H)

I-5-6   4-F   H   Me   t-Bu   Na   93-110
MS(m/e, FAB): 447(M⁺+Na), 253
NMR(in d₆-DMSO) δ ppm:
1.37(s,9H), 1.2~1.5(m,2H), 1.9~2.1(m, 2H), 2.52(s,3H), 3.0~3.4(m,2H), 3.6~ 3.9(m,1H), 4.1~4.4(m,1H), 5.68(d,d,1H, J=7Hz,16Hz), 6.4(d,1H,J=16Hz), 7.1~ 7.3(m,4H)

I-5-7   4-Br   H   Me   Ph   Na   118-122
MS(m/e, FAB): 527(M⁺+Na), 505(M⁺+H), 413, 329, 176
NMR(in d₆-DMSO) δ ppm:
1.2~1.6(m,2H), 1.8~2.2(m,2H), 2.64(s, 3H), 3.0~3.5(m,2H), 3.6~3.9(m,1H), 4.1~ 4.4(m,1H), 5.78(d,d,1H,J=7Hz,16Hz), 6.53(d,1H,J=16Hz), 7.4~8.6(m,9H)

I-5-8   4-F   H   i-Pr   Ph   Na   121-127
MS(m/e, FAB): 495(M⁺+Na), 472(M⁺), 413, 317
NMR(in d₆-DMSO) δ ppm:
1.2~1.6(m,2H), 1.32(d,6H,J=7Hz), 1.8~ 2.2(m,2H), 3.54(Heptaplet,1H,J=7Hz), 3.4~4.1(m,3H), 4.1~4.4(m,1H), 5.63(d, d,1H,J=7Hz,16Hz), 6.61(d,1H,J=16Hz), 7.1~ 8.6(m,9H)

I-5-9   4-F   H   n-Pr   Ph   Na   115-125
MS(m/e, FAB): 495(M⁺+Na), 473(M⁺+H), 413, 255
NMR(in d₆-DMSO) δ ppm:

TABLE 16-continued

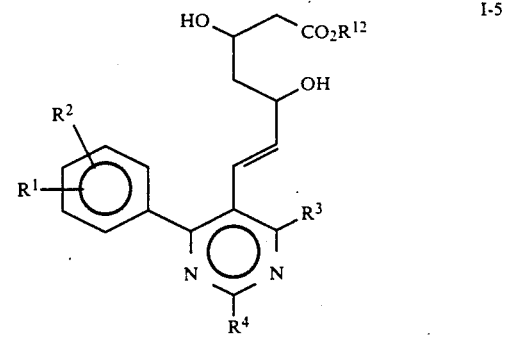

I-5

| Compound | R¹ | R² | R³ | R⁴ | R¹² | m.p. (°C.) |
|---|---|---|---|---|---|---|

1.01(t,3H,J=7Hz), 1.2~1.6(m,2H), 1.7~
2.2(m,4H), 2.8~3.1(m,2H), 3.0~3.5(m,2H),
3.5~4.0(m,1H), 4.1~4.5(m,1H), 5.67(d,
d,1H,J=7Hz,16Hz), 6.56(d,1H,J=16Hz), 7.1~
8.7(m,9H)

| I-5-10 | 4-F | H | 1-Pr | 4-Me—Ph | Na | 115-120 |

MS(m/e, FAB): 509(M⁺ +Na), 487(M⁺ +H)
NMR(in d₆-DMSO) δ ppm:
1.2~1.6(m,2H), 1.31(d,6H,J=7Hz), 1.8~
2.1(m,2H), 2.38(s,3H), 3.4~4.0(m,3H),
3.51(Heptaplet,1H,J=7Hz), 4.1~4.4(m,1H),
5.60(d,d,1H,J=7Hz,16Hz), 6.59(d,1H,J=16
Hz), 7.1~8.5(m,8H)

| I-5-11 | 4-F | H | cyclo-Pr | Ph | Na | 204-208 |

MS(m/e, FAB): 493(M⁺ +Na), 471(M⁺ +H)
NMR(in d₆-DMSO) δ ppm:
1.0~2.2(m,8H), 2.3~2.7(m,1H), 3.4~4.0
(m,3H), 4.1~4.4(m,1H), 5.85(d,d,1H,J=6
Hz,17Hz), 6.60(d,1H,J=17Hz), 7.1~8.5(m,
9H)

| I-5-12 | 4-F | H | cyclo-Pr | CH₂Ph | Na | 135-148 |

MS(m/e, FAB): 507(M⁺ +Na), 485(M⁺ +H), 329
NMR(in d₆-DMSO) δ ppm:
0.7~1.2 (m,4H), 1.2~1.6(m,2H), 1.8~2.1
(m,2H), 2.3~2.6(m,1H), 2.9~3.5(m,2H),
3.5~4.0(m,1H), 4.09(s,2H), 4.1~4.5(m,1H),
5.73(d,d,1H,J=16Hz), 6.50(d,1H,J=16Hz),
7.0~8.30(m,9H)

| I-5-13 | 4-F | H | cyclo-Pr | 3-Cl—Ph | Na | 143-147 |

MS(m/e, FAB): 527(M⁺ +Na), 505(M⁺ +H), 413,
329
NMR(d₆-DMSO ) δ ppm:
0.9~1.4(m,4H), 1.3~1.7(m,2H), 1.8~2.2
(m,2H), 2.3~2.7(m,1H), 2.9~3.7(m,2H),
3.5~4.0(m,1H), 4.1~4.5(m,1H), 5.85(d,d,
1H,J=6Hz,16Hz), 6.60(d,1H,J=16Hz),
7.0~8.5(m,8H)

| I-5-14 | 4-F | H | cyclo-Pr | 4-MeO—Ph | Na | 152-178 |

MS(m/e, FAB): 523(M⁺ +Na), 501(M⁺ +H), 329
NMR (d₆-DMSO ) δ ppm:
1.0~1.4(m,4H), 1.3~1.7(m,2H), 1.8~2.2
(m,2H), 2.3~2.7(m,1H), 3.0~4.0(m,3H),
3.83(s,3H), 4.1~4.5(m,1H), 5.80(d,d,1H,
J=6Hz,16Hz), 6.58(d,1H,J=16Hz), 6.9~8.4
(m,8H)

| I-5-15 | 4-F | H | cyclo-Pr | 4-Me—Ph | Na | 155-157 |

MS(m/e, FAB): 507(M⁺ +Na), 485(M⁺ +H), 413,
329
NMR (in d₆-DMSO) δ ppm:
0.9~1.7(m,6H), 1.8~2.2(m,2H), 2.2~2.7
(m,1H), 2.37(s,3H), 2.8~3.5(m,2H),
3.5~4.0(m,1H), 4.1~4.5(m,1H), 5.82(d,d,
1H,J=6Hz,16Hz), 6.60(d,1H,J=16Hz),
7.1~8.5(m,8H)

| I-5-16 | 4-F | H | cyclo-Pr | 4-Ph—Ph | Na | 192-207 |

MS(m/e, FAB): 569(M⁺ +Na), 547(M⁺ +H), 307,
154
NMR (in d₆-DMSO) δ ppm:
0.9~1.7(m,6H), 1.8~2.2(m,2H), 2.3~2.7
(m,1H), 2.8~3.6(m,2H), 3.5~4.0(m,1H),
4.1~4.5(m,1H), 5.86(d,d,1H,J=6Hz,16Hz),
6.62(d,1H,J=16Hz), 7.1~8.6(m,13H)

| I-5-17 | 4-F | H | cyclo-Pr | 3-CF₃—Ph | Na | 147-151 |

MS(m/e, FAB): 561(M⁺ +Na), 383, 199
NMR (in d₆-DMSO) δ ppm:
0.9~1.7(m,6H), 1.8~2.1(m,2H), 2.3~2.7
(m,1H), 2.8~3.5(m,2H), 3.5~4.0(m,1H),
4.1~4.5(m,1H), 5.86(d,d,1H,J=6Hz,16Hz),
6.61(d,1H,J=16Hz), 7.1~8.8(m,8H)

Compound I-3-8 was prepared by the process of the following Example 2 (2-h, 2-j).

EXAMPLE 2-h (E)-3,5-dihydroxy-7-[4'-(4'-fluorophenyl)-6'-(1'-methylethyl)-2'-phenylpyrimidin-5'-yl]hept-6-enoic acid (compound I-2-8)

213 mg (4.44×10⁻⁴ mol) of compound I-1-8 was dissolved in 10 ml of ethanol. Then, 0.84 ml of a 0.5N sodium hydroxide aqueous solution was dropwise added thereto. The mixture was stirred at room temperature for further 2 hours. Then, ethanol was distilled off at 45° C. under reduced pressure, and 5 ml of distilled water was added thereto. The remaining starting material was extracted with ethyl ether. The aqueous phase was adjusted to pH2 by an addition of 0.1 ml of 2N hydrochloric acid. The reaction solution was extracted with ethyl ether, and the extract was washed with a saturated sodium chloride aqueous solution and dried over anhydrous magnesium sulfate. Then, the solvent was distilled off to obtain 190 mg (95.1%) of the desired product as colorless powder. Melting point: 52°-58° C.

EXAMPLE 2-j (E)-6-[4'-(4''-fluorophenyl)-6'-(1''-methylethyl)-2'-phenylpyrimidin-5'-ylethenyl]-4-hydroxy-3,4,5,6-tetrahydro-2H-pyran-2-one (compound I-3-8)

190 mg 4.22×10⁻⁴ mol) of compound I-2-8 was dissolved in 2 ml of dry methylene chloride dehydrated by molecular sieve. Then, 220 mg (5.19×10⁻⁴ mol) of N-cyclohexyl-N'-[2-(methylmorpholinium)ethyl]carbodiimide p-toluene sulfonate (lactone-forming agent) was added thereto, and the mixture was stirred at room temperature for 5 hours. Then, 200 mg of the lactone-forming agent was further added, and the mixture was stirred at room temperature overnight. The reaction solution was washed with water and then with a saturated sodium chloride aqueous solution and dried over anhydrous magnesium sulfate. Then, the solvent was distilled off under reduced pressure, and the residue was purified by silica gel chromatography (eluent: 10% ethyl acetate/benzene) to obtain 120 mg (yield: 65.8%) of the desired product as colorless powder. Melting point: 177°-180° C. This compound was a mixture of two types of lactones (trans, cis) attributable to the two diastereomers (a mixture of erythro and threo) of I-2-8 used as the starting material. However, from the result of the thin layer chromatography analysis (silica gel; developing solvent: methyl-t-butyl ether/n-hexane/acetone=7/2/1 (v/v)) and of the NMR analysis, this product was substantially pure trans-lactone.

MS(m/e): 432(M+), 414, 317, 248,

NMR (in CDCl$_3$) δ ppm: 1.35, 1.36(d×2, 6H, J=7Hz), 1.5-1.7(m, 2H), 2.6-2.8(m, 2H), 3.39(m, 1H, J=7Hz), 4.2-4.4(m, 2 H), 5.2-5.3(m, 1H), 5.54(d, d, 1H, J=6Hz, 17Hz), 6.80(d, 1H, J=6Hz), 7.1-8.6(m, 9H)

Compound I-6-8 was prepared by the process of the following Example 2-n.

EXAMPLE 2-n

Ethyl (E)-7-[4'-(4''-fluorophenyl)-6'-(1'''-methylethyl)-2'-phenylpyrimidin-5'-yl]-3-hydroxy-5-oxo-6-heptenoate (compound I-6-8)

100 mg (2.09×10$^{-4}$ mol) of compound I-1-8 was dissolved in 5 ml of dry toluene dehydrated by molecular sieve. Then, 360 mg of activated manganese dioxide was added thereto, and the mixture was stirred at room temperature for 3 days. 10 ml of benzene was added to the reaction solution, and manganese dioxide was removed by filtration with celite. A filtrate was decolored with activated charcoal, and then the solvent was distilled off. The residual oil was purified by silica gel column chromatography (eluent: benzene/ethyl acetate) to obtain 65 mg (65.3%) of the desired product as slightly yellow powder. Melting point: 47°-51° C.

MS(m/e): 476(M+), 458, 415 NMR(in CDCl$_3$) δ ppm: 1.2-1.5(d+t, 9H, J=7Hz), 2.3-2.8(m, 4H), 3.3-3.5 (m, 1H), 4.13(q, 2H, J=7Hz), 4.3-4.6(m×2, 2H), 6.24(d, 1H, J=16Hz), 7.1-8.7(m, 10H)

FORMULATION EXAMPLE 1

| Tablets | |
|---|---|
| Compound I-5-14 | 1.0 g |
| Lactose | 5.0 g |
| Crystal cellulose powder | 8.0 g |
| Corn starch | 3.0 g |
| Hydroxypropyl cellulose | 1.0 g |
| CMC-Ca | 1.5 g |
| Magnesium stearate | 0.5 g |
| Total | 20.0 g |

The above components were mixed by a usual method and then tabletted to produce 100 tablets each containing 10 mg of the active ingredient.

FORMULATION EXAMPLE 2

| Capsules | |
|---|---|
| Compound I-5-14 | 1.0 g |
| Lactose | 3.5 g |
| Crystal cellulose powder | 10.0 g |
| Magnesium stearate | 0.5 g |
| Total | 15.0 g |

The above components were mixed by a usual method and then packed in No. 4 gelatin capsules to obtain 100 capsules each containing 10 mg of the active ingredient.

FORMULATION EXAMPLE 3

| Soft capsules | |
|---|---|
| Compound I-5-14 | 1.00 g |
| PEG (polyethylene glycol) 400 | 3.89 g |
| Saturated fatty acid triglyceride | 15.00 g |
| Peppermint oil | 0.01 g |
| Polysorbate 80 | 0.10 g |
| Total | 20.00 g |

The above components were mixed and packed in No. 3 soft gelatin capsules by a usual method to obtain 100 soft capsules each containing 10 mg of the active ingredient.

FORMULATION EXAMPLE 4

| Ointment | |
|---|---|
| Compound I-5-14 | 1.0 g (10.0 g) |
| Liquid paraffin | 10.0 g (10.0 g) |
| Cetanol | 20.0 g (20.0 g) |
| White vaseline | 68.4 g (59.4 g) |
| Ethylparaben | 0.1 g (0.1 g) |
| L-menthol | 0.5 g (0.5 g) |
| Total | 100.0 g |

The above components were mixed by a usual method to obtain a 1% (10%) ointment.

FORMULATION EXAMPLE 5

| Suppository | |
|---|---|
| Compound I-5-14 | 1.0 g |
| Witepsol H15* | 46.9 g |
| Witepsol W35* | 52.0 g |
| Polysorbate 80 | 0.1 g |
| Total | 100.0 g |

*Trademark for triglyceride compound

The above components were melt-mixed by a usual method and poured into suppository containers, followed by cooling for solidification to obtain 100 suppositories of 1 g each containing 10 mg of the active component.

FORMULATION EXAMPLE 6

| Injection formulation | |
|---|---|
| Compound I-5-14 | 1 mg |
| Distilled water for injection formulation | 5 ml |

The formulation is prepared by dissolving the compound in the distilled water whenever it is required.

FORMULATION EXAMPLE 7

| Granules | |
|---|---|
| Compound I-5-14 | 1.0 g |
| Lactose | 6.0 g |
| Crystal cellulose powder | 6.5 g |
| Corn starch | 5.0 g |
| Hydroxypropyl cellulose | 1.0 g |
| Magnesium stearate | 0.5 g |
| Total | 20.0 g |

The above components were granulated by a usual method and packaged to obtain 100 packages each containing 200 mg of the granules so that each package contains 10 mg of the active ingredient.

We claim:

1. A compound of the formula:

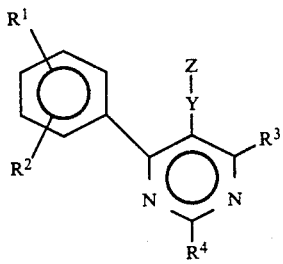

(I)

wherein $R^1$ and $R^2$ are independently hydrogen, $C_{1-6}$ alkyl, $C_{3-6}$ cycloalkyl, $C_{1-3}$ alkoxy, n-butoxy, i-butoxy, sec-butoxy, $R^5R^6N-$ (wherein $R^5$ and $R^6$ are independently hydrogen or $C_{1-3}$ alkyl), trifluoromethyl, trifluoromethoxy, difluoromethoxy, fluoro, chloro, bromo, phenyl, phenoxy, benzyloxy, hydroxy, trimethylsilyloxy, diphenyl-t-butylsilyloxy, hydroxymethyl or $-O(CH_2)_lOR^{15}$ (wherein $R^{15}$ is hydrogen or $C_{1-3}$ alkyl, and l is 1, 2 or 3); or when located at the ortho position to each other, $R^1$ and $R^2$ together form $-CH=CH-CH=CH-$ or methylene dioxy; Y is $-CH_2-$, $-CH_2CH_2-$, $-CH=CH-$, $-CH_2-CH=CH-$ or $-CH=CH-CH_2$; Z is $-Q-CH_2WCH_2-CO_2R^{12}$,

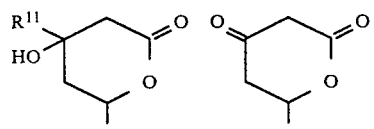

or

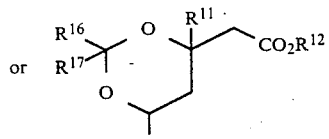

(wherein Q is $-C(O)-$, $-C(OR^{13})_2-$ or $-CH(OH)-$, proviso that when Z is

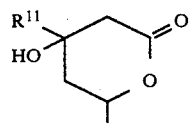

then Y is not $-CH_2CH_2-$ or $-CH=CH-$; W is $-C(O)-$, $-C(OR^{13})_2-$ or $-C(R^{11})(OH)-$; $R^{11}$ is hydrogen or $C_{1-3}$ alkyl; $R^{12}$ is hydrogen or $R^{14}$ (wherein $R^{14}$ is physiologically hydrolyzable alkyl or M (wherein M is $NH_4$, sodium, potassium, ½ calcium or a hydrate of lower alkylamine, di-lower alkylamine or tri-lower alkylamine)); two $R^{13}$ are independently primary or secondary $C_{1-6}$ alkyl; or two $R^{13}$ together form $-(CH_2)_2-$ or $-(CH_2)_3-$; $R^{16}$ and $R^{17}$ *are independently hydrogen or $C_{1-3}$* alkyl; $R^3$ is hydrogen, $C_{1-6}$ alkyl, $C_{2-3}$ alkenyl, $C_{3-6}$ cycloalkyl,

(wherein $R^7$ is hydrogen, $C_{1-4}$ alkyl, $C_{1-3}$ alkoxy, fluoro, chloro, bromo or trifluoromethyl), phenyl-$(CH_2)_m-$ (wherein m is 1, 2 or 3), $-(CH_2)_nCH(CH_3)$-phenyl or phenyl-$(CH_2)_nCH(CH_3)-$ (wherein n is 0, 1 or 2; $R^4$ is $C_{1-8}$ alkyl, $C_{3-7}$ cycloalkyl, α- or β- naphthyl, 2-, 3-, or 4-pyridyl,

(wherein $R^8$, $R^9$ and $R^{10}$ are independently hydrogen, $C_{1-4}$ alkyl, $C_{1-8}$ alkoxy, $C_{1-3}$ alkylthio, chloro, bromo, fluoro, $-NR^{18}R^{19}$ (wherein $R^{18}$ and $R^{19}$ are independently $C_{1-3}$ alkyl), trichloromethyl, trifluoromethyl, trifluoromethoxy, difluoromethoxy, phenoxy, benzyloxy, hydroxy, trimethylsilyloxy, diphenyl-t-butysilyloxy, hydroxymethyl or $-O(CH_2)_kOR^{20}$ (wherein $R^{20}$ is hydrogen or $C_{1-3}$ alkyl, and k is 1, 2 or 3); when $R^9$ and $R^{10}$ are hydrogen at the same time, $R^8$ is

(wherein $R^{25}$ is hydrogen, $C_{1-4}$ alkyl, $C_{1-3}$ alkoxy, chloro, bromo, or fluoro)) or $C_{1-3}$ alkyl substituted by 1 member selected from the group consisting of

(wherein $R^8$, $R^9$ and $R^{10}$ are as defined above) and naphthyl and by 0, 1 or 2 members selected from the group consisting of $C_{1-8}$ alkyl.

2. The compound according to claim 1, wherein in the formula I, when $R^2$ is hydrogen, $R^1$ is hydrogen, 3'-fluoro, 3'-chloro, 3'-methyl, 4'-methyl, 4'-chloro or 4'-fluoro; or $R^1$ and $R^2$ together represent 3'-methyl-4'-chloro, 3',5'-dichloro, 3',5'-difluoro, 3',5'-dimethyl or 3'-methyl-4'-fluoro; $R^3$ is primary or secondary $C_{1-6}$ alkyl or $C_{3-6}$ cycloalkyl; $R^4$ is $C_{1-8}$ alkyl, $C_{3-7}$ cycloalkyl, α- or β- naphthyl, 2-, 3- or 4-pyridyl,

(wherein $R^8$, $R^9$ and $R^{10}$ are independently hydrogen, $C_{1-4}$ alkyl, $C_{1-8}$ alkoxy, chloro, bromo, fluoro, dimethylamino, trifluoromethyl, hydroxy, phenoxy, benzyloxy, trimethylsilyloxy, diphenyl-t-butylsilyloxy, methylenedioxy (in this case, $R^{10}$ is hydrogen), hydroxymethyl or when $R^9$ and $R^{10}$ are hydrogen at the same time, $R^8$ is

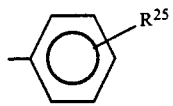

(wherein $R^{25}$ is hydrogen, $C_{1-4}$ alkyl, $C_{1-3}$ alkoxy, chloro, bromo or fluoro)) or

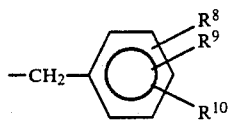

(wherein $R^8$, $R^9$ and $R^{10}$ are as defined above); Y is $-CH_2-CH_2-$ or $-CH=CH-$; Z is

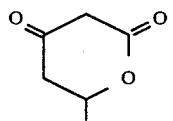

$-CH(OH)CH_2CH(OH)CH_2CO_2R^{12}$, $-CH(OH)CH_2-C(O)CH_2CO_2R^{12}$ or $-CH(OH)CH_2C(OR^{13})_2CH_2CO_2R^{12}$.

3. The compound according to claim 2, wherein $R^2$ is hydrogen, $R^1$ is hydrogen, 4'-methyl, 4'-chloro or 4'-fluoro; or $R^1$ and $R^2$ together form 3', 5'-dimethyl or 3'-methyl-4'-fluoro; $R^4$ is other than $C_{1-8}$ alkyl, $C_{3-7}$ cycloalkyl, α- or β-napthyl and 2-, 3- or 4-pyridyl; Y is $-CH_2-CH_2-$ or (E)—$CH=CH-$.

4. The compound according to claim 2, wherein when $R^2$ is hydrogen, $R^1$ is hydrogen, 4'-chloro or 4'-fluoro; or $R^1$ and $R^2$ together represent 3'-methyl-4'-fluoro; $R^3$ is ethyl, n-propyl, i-propyl or cyclopropyl; $R^4$ is

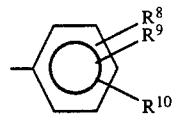

(wherein $R^8$, $R^9$ and $R^{10}$ are independently hydrogen, methyl, ethyl, n-propyl, i-propyl, n-butyl, t-butyl, methoxy, ethoxy, n-propoxy, i-propoxy, chloro, bromo, fluoro, trifluoromethyl, hydroxy, trimethylsilyloxy, diphenyl-t-butylsilyloxy, methylenedioxy (in this case, $R^{10}$ is hydrogen), hydroxymethyl or phenyl), or benzyl; and Y is (E)—$CH=CH-$.

5. The compound according to claim 1, wherein $R^3$ is cyclopropyl.

6. The compound according to claim 1 wherein when $R^{10}$ is hydrogen and when located at the ortho position to each other, $R^8$ and $R^9$ together form $-OC(R^{23})(R^{24})O-$; wherein $R^{23}$ and $R^{24}$ are independently hydrogen or $C_{1-3}$ alkyl.

7. The compound according to claim 2, wherein $R^1$ is hydrogen 4'-chloro or 4'-fluoro; $R^2$ is hydrogen; $R^3$ is i-propyl or cyclopropy; $R^4$ is phenyl, 3'-chlorophenyl, 4'-chlorophenyl, 3'-tolyl, 4'-tolyl, 3'-methoxyphenyl, 4'methoxyphenyl, 3'-trifluoromethylphenyl, 4'-trifluoromethylphenyl or 3', 4'-dimethoxypheny; and Y is (E)—$CH=CH-$.

8. The compound according to claim 1, which is (E)-3,5-dihydroxy-7-[4'-(4''-fluorophenyl)-6'-(1''-methylethyl)-2 '-(4''-tolyl)pyrimidin-5'-yl]hept-6-enoic acid, or a sodium salt or $C_{1-3}$ alkyl ester of the carboxylic acid.

9. The compound according to claim 1, which is (E)-3,5-dihydroxy-7-[4'-(4''-fluorophenyl)-6'-(1''-methylethyl)-2 '-phenylpyrimidin-5'-yl]hept-6-enoic acid, or a sodium salt or $C_{1-3}$ alkyl ester of the carboxylic acid.

10. The compound according to claim 1, which is (E)-3,5-dihydroxy-7-[2'-(3''-chlorophenyl)-4'-(4''-fluorophenyl)-6 '-(1''-methylethyl)pyrimidin-5'-yl]-hept-6-enoic acid, or a sodium salt or $C_{1-3}$ alkyl ester of the carboxylic acid.

11. The compound according to claim 1, which is (E)-3,5-dihydroxy-7-[4'-(4''-fluorophenyl)-2'-(4''-methoxyphenyl)-6 '-(1''-methylethyl)pyrimidin-5'-yl]-hept-6-enoic acid, or a sodium salt or $C_{1-3}$ alkyl ester of the carboxylic acid.

12. The compound according to claim 1, which is (E)-3,5-dihydroxy-7-[4'-(4''-fluorophenyl)-6'-(1''-methylethyl)-2 '-(3''-trifluoromethylphenyl)pyrimidin-5'-yl]hept-6-enoic acid, or a sodium salt or $C_{1-3}$ alkyl ester of the carboxylic acid.

13. The compound according to claim 1, which is (E)-3,5-dihydroxy-7-[4'-cyclopropyl-6'-(4''-fluorophenyl)-2'-(4 ''-tolyl)pyrimidin-5'-yl]-hept-6-enoic acid, or a sodium salt or $C_{1-3}$ alkyl ester of the carboxylic acid.

14. The compound according to claim 1, which is (E)-3,5-dihydroxy-7-[4'-cyclopropyl-6'-(4''-fluorophenyl)-2 '-phenylpyrimidin-5'-yl]hept-6-enoic acid, or a sodium salt or $C_{1-3}$ alkyl ester of the carboxylic acid.

15. The compound according to claim 1, which is (E)-3,5-dihydroxy-7 [2'-(3''-chlorophenyl)-4'-cyclopropyl-6 '-(4''-fluorophenyl)pyrimidin-5'-yl]hept-6-enoic acid, or a sodium salt or $C_{1-3}$ alkyl ester of the carboxylic acid.

16. The compound according to claim 1, which is (E)-3,5-dihydroxy-7-[4'-cyclopropyl-6'-(4''-fluorophenyl)-2'-(4''-methoxyphenyl)pyrimidin-5'yl]help-6-enoic acid, or a sodium salt or $C_{1-3}$ alkyl ester of the carboxylic acid.

17. The compound according to claim 1, which is (E)-3,5-dihydroxy-7-[4'-cyclopropyl-6'-(4''-fluorophenyl)-2'-(3''-trifluoromethylphenyl)-pyrimidin-5 '-yl]-hept-6-enoic acid, or a sodium salt or $C_{1-3}$ alkyl ester of the carboxylic acid.

18. The compound according to claim 1, which is (E)-3,5-dihydroxy-7-[4'-(1''-methylethyl)-6'-phenyl-2'-(4''-tolyl) pyrimidin-5'-yl]hept-6-enoic acid, or a sodium salt or $C_{1-3}$ alkyl ester of the carboxylic acid.

19. The compound according to claim 1, which is (E)-3,5-dihydroxy-7-[2',6'-diphenyl-4'-(1''-methylethyl)-pyrimidin-5 '-yl]hept-6-enoic acid, or a sodium salt or $C_{1-3}$ alkyl ester of the carboxylic acid.

20. The compound according to claim 1, which is (E)-3,5-dihydroxy-7-[2'-(3''-chlorophenyl)-4'-(1''-methylethyl)-6 '-phenylpyrimidin-5'-yl]hept-6-enoic acid, or a sodium salt or $C_{1-3}$ alkyl ester of the carboxylic acid.

21. The compound according to claim 1, which is (E)-3,5-dihydroxy-7-[2'-(4''-methoxyphenyl)-4'-(1''-methylethyl)-6 '-phenylpyrimidin-5'-yl]hept-6-enoic acid, or a sodium salt or $C_{1-3}$ alkyl ester of the carboxylic acid.

22. The compound according to claim 1, which is (E)-3,5-dihydroxy-7-[4'-(1''-methylethyl)-6'-phenyl2'-(3''-trifluoromethylphenyl)pyrimidin-5'-yl]hept-6-enoic acid, or a sodium salt or $C_{1-3}$ alkyl ester of the carboxylic acid.

23. The compound according to claim 1, which is (E)-3,5-dihydroxy-7-[4'-cyclopropyl-6'-phenyl-2'-(4''-tolyl) pyrimidin-5'-yl]hept-6-enoic acid, or a sodium salt or $C_{1-3}$ alkyl ester of the carboxylic acid.

24. The compound according to claim 1, which is (E)-3,5-dihydroxy-7-[4'-cyclopropyl-2',6'-diphenyl-pyrimidin-5'-yl]hept-6-enoic acid, or a sodium salt or $C_{1-3}$ alkyl ester of the carboxylic acid.

25. The compound according to claim 1, which is (E)-3,5-dihydroxy-7-[2'-(3''-chlorophenyl)-4'-cyclopropyl-6'-phenylpyrimidin-5'-yl]hept-6-enoic acid, or a sodium salt or $C_{1-3}$ alkyl ester of the carboxylic acid.

26. The compound according to claim 1, which is (E)-3,5-dihydroxy-7 [4'-cyclopropyl-2'-(4''-methoxyphenyl)6'-phenylpyrimidin-5'-yl]hept-6-enoic acid, or a sodium salt or $C_{1-3}$ alkyl ester of the carboxylic acid.

27. The compound according to claim 1, which is (E)-3,5-dihydroxy-7-[4'-cyclopropyl-6'-phenyl-2'-(3''-trifluoromethylphenyl) pyrimidin-5'-yl]hept-6-enoic acid, or a sodium salt or $C_{1-3}$ alkyl ester of the carboxylic acid.

28. The compound according to claim 1, which is (E)-3,5-dihydroxy-7-[4'-(4''-chlorophenyl)-6'-(1''-methylethyl)-2 '-(4''-tolyl)pyrimidin-5'-yl]hept-6-enoic acid, or a sodium salt or $C_{1-3}$ alkyl ester of the carboxylic acid.

29. The compound according to claim 1, which is (E)-3,5-dlhydroxy-7-[4'-(4''-chlorophenyl)-6'-(1''-methylethyl)-2 '-phenylpyrimidin-5'-yl]hept-6-enoic acid, or a sodium salt or $C_{1-3}$ alkyl ester of the carboxylic acid.

30. The compound according to claim 1, which is (E)-3,5-dihydroxy-7-[2'-(3''-chlorophenyl)-4'-(4''-chlorophenyl)-6 '-(1''-methylethyl)pyrimidin-5'-yl]-hept-6-enoic acid, or a sodium salt or $C_{1-3}$ alkyl ester of the carboxylic acid.

31. The compound according to claim 1, which is (E)-3,5-dihydroxy-7-[4'-(4''-chlorophenyl)-6'-cyclopropyl-2'(4''-tolyl) pyrimidin-5'-yl]hept-6-enoic acid, or a sodium salt or $C_{1-3}$ alkyl ester of the carboxylic acid.

32. The compound according to claim 1, which is (E)-3,5-dihydroxy-7-[4'-(4''-chlorophenyl)-6'-cyclopropyl2'-phenylpyrimidin-5 '-yl]hept-6-enoic acid, or a sodium salt or $C_{1-3}$ alkyl ester of the carboxylic acid.

33. The compound according to claim 1, which is (E)-3,5-dihydroxy-7-[2'-(3''-chlorophenyl)-4'-(4''-chlorophenyl)-6 '-cyclopropylpyrimidin-5'-yl]hept 6-enoic acid, or a sodium salt or $C_{1-3}$ alkyl ester of the carboxylic acid.

34. An anti-hyperlipidemia composition containing an effective amount of the compound of formula I, as defined in claim 1, and a pharmaceutically acceptable carrier.

35. An anti-hyperlipoproteinemia composition containing an effective amount of the compound of formula I as defined in claim 1, and a pharmaceutically acceptable carrier.

36. An anti-atherosclerosis composition containing an effective amount of the compound of formula I, as defined in claim 1, and a pharmaceutically acceptable carrier.

37. A method for reducing hyperlipidemia, hyperlipoproteinemia or atherosclerosis, which comprises administering an effective amount of the compound of the formula I as defined in claim 1.

* * * * *

UNITED STATES PATENT AND TRADEMARK OFFICE
CERTIFICATE OF CORRECTION

PATENT NO. : 5,026,708

DATED : June 25, 1991

INVENTOR(S) : FUJIKAWA ET AL.

It is certified that error appears in the above-identified patent and that said Letters Patent is hereby corrected as shown below:

Column 41, line 65, change "hydrogen 4'-chloro" to -- hydrogen, 4'-chloro --.

Column 41, line 66, change "cyclopropy" to -- cyclopropyl --.

Column 41, line 68, change "4'methoxyphenyl" to -- 4'-methoxyphenyl --.

Column 42, line 1, change "3',4'-dimethoxypheny" to -- 3',4'-dimethoxyphenyl --.

Column 42, line 31, change "5'-yl]-hept-6-enoic" to -- 5'-yl]hept-6-enoic --.

Column 42, line 39, change "(E)-3,5-dihydroxy-7" to -- (E)-3,5-dihydroxy-7- --.

UNITED STATES PATENT AND TRADEMARK OFFICE
CERTIFICATE OF CORRECTION

PATENT NO. : 5,026,708

DATED : June 25, 1991

INVENTOR(S) : FUJIKAWA ET AL.

It is certified that error appears in the above-identified patent and that said Letters Patent is hereby corrected as shown below:

Column 42, line 45, change "phenyl)-2'-(4''-methoxyphenyl)pyrimidin -5'yl]help-6-" to -- phenyl)-2'-(4''-methoxyphenyl)pyrimidine-5'-yl]hept-6- --

Column 43, line 21, change "(E)-3,5-dihydroxy-7" to -- (E)-3,5-dihydroxy-7- --.

Column 43, line 35, change "(E)-3,5-dlhydroxy-7-" to -- (E)-3,5-dihydroxy-7- --.

Column 44, line 10, change "pyl-2'(4''-tolyl)" to -- pyl-2'-(4''-tolyl) --.

UNITED STATES PATENT AND TRADEMARK OFFICE
CERTIFICATE OF CORRECTION

PATENT NO. : 5,026,708

DATED : June 25, 1991

INVENTOR(S) : Fujikawa et al

It is certified that error appears in the above-identified patent and that said Letters Patent is hereby corrected as shown below:

Column 44, line 14, change "propgel2'-" to --poropyl-2'- --.

Signed and Sealed this

Twenty-sixth Day of January, 1993

Attest:

STEPHEN G. KUNIN

Attesting Officer

Acting Commissioner of Patents and Trademarks